US010349639B2

(12) United States Patent
Telugu et al.

(10) Patent No.: US 10,349,639 B2
(45) Date of Patent: Jul. 16, 2019

(54) TARGETED GENOME EDITING IN ZYGOTES OF DOMESTIC LARGE ANIMALS

(71) Applicant: University of Maryland, College Park, College Park, MD (US)

(72) Inventors: Bhanu Prakash V. L. Telugu, College Park, MD (US); Ki-Eun Park, College Park, MD (US)

(73) Assignee: University of Maryland, College Park, College Park, MD (US)

( * ) Notice: Subject to any disclaimer, the term of this patent is extended or adjusted under 35 U.S.C. 154(b) by 118 days.

(21) Appl. No.: 15/128,595

(22) PCT Filed: Mar. 26, 2015

(86) PCT No.: PCT/US2015/022660
§ 371 (c)(1),
(2) Date: Sep. 23, 2016

(87) PCT Pub. No.: WO2015/148761
PCT Pub. Date: Oct. 1, 2015

(65) Prior Publication Data

US 2017/0172119 A1 Jun. 22, 2017

Related U.S. Application Data

(60) Provisional application No. 61/970,794, filed on Mar. 26, 2014.

(51) Int. Cl.

*A01K 67/027* (2006.01)
*C12N 15/90* (2006.01)
*A61D 19/04* (2006.01)
*C07K 14/47* (2006.01)
*C12Q 1/6876* (2018.01)

(52) U.S. Cl.

CPC .......... *A01K 67/0275* (2013.01); *A61D 19/04* (2013.01); *C07K 14/4703* (2013.01); *C12N 15/907* (2013.01); *C12Q 1/6876* (2013.01); *A01K 2217/072* (2013.01); *A01K 2227/108* (2013.01); *C12Q 2600/124* (2013.01)

(58) Field of Classification Search

CPC .................................................. A01K 67/0275
See application file for complete search history.

(56) References Cited

U.S. PATENT DOCUMENTS

2012/0276537 A1 11/2012 Kuhn et al.
2014/0041066 A1* 2/2014 Carlson .............. A01K 67/0275 800/14

FOREIGN PATENT DOCUMENTS

WO 2014022120 A1 2/2014
WO 2015030881 A1 3/2015

OTHER PUBLICATIONS

Yang et al. "One-step generation of mice carrying reporter and conditional alleles by CRISPR/Cas-mediated genome engineering" Cell. Sep. 12, 2013; 154(6); 1370-1379 (Year: 2013).*
Yang et al. (Cell. Sep. 12, 2013; 154(6): 1370-1379). (Year: 2013).*
Aida, Tomomi et al., "Translating Human Genetics into Mouse: The Impact of Ultra-Rapid in vivo Genome Editing", Review Article in Development, Growth & Differentiation (2014) vol. 56, pp. 34-45.
Hai, et al., "One-Step Generation of Knockout Pigs by Zygote Injection of CRISPR/Cas System" Cell research, Jan. 31, 2014, 24: pp. 372-375.
Yang, et al., "One-Step Generation of Mice Carrying Reporter and Conditional Alleles by CRISPR/Cas-Mediated Genome Engineering", Cell, Sep. 12, 2013, 154, pp. 1370-1379.
University of Maryland, PCT/US2015/022660 filed Mar. 26, 2015, "International Preliminary Report on Patentability" dated Oct. 6, 2016.
University of Maryland, PCT/US2015/022660 filed Mar. 26, 2015, "The International Search Report and The Written Opinion of the International Searching Authority" dated Aug. 13, 2015.
Xiaoping, Li, et al., "Rosa26-targeted Swine Models for Stable Gene Over-Expression and Cre-mediated Lineage Tracing", Cell Research, pp. 501-504 published online, Feb. 7, 2014.
Zoltán, Ivics, et al., "Germline Transgenesis in Pigs by Cytoplasmic Microinjection of Sleeping Beauty Transposons", Nature Protocols, vol. 9, No. 4, pp. 810-827, published online, Mar. 13, 2014.
Fan, Nana, et al., "Genetically Modified Pig Models for Human Diseases", Journal of Genetics and Genomics, pp. 67-73, available online, Jan. 8, 2013.
Markljung, Ellen, et al., "ZBED6, a Novel Transcription Factor Derived from a Domesticated DNA Transposon Regulates IGF2 Expression and Muscle Growth", PloS Biology, vol. 7, Issue 12, pp. 1-14, published Dec. 15, 2009.
Park et al., "Targeted gene knock-in by CRISPR/Cas ribonucleoproteins in porcine zygotes", www.nature.com/scientificreports, 10 pages, Feb. 14, 2017.
Ran et al., "Genome engineering using the CRISPR-Cas9 system", Nature Protocols, vol. 8, No. 11, pp. 2281-2308, Oct. 24, 2013.

* cited by examiner

*Primary Examiner* — Scott Long
(74) *Attorney, Agent, or Firm* — McKee, Voorhees & Sease, PLC

(57) ABSTRACT

A method is provided of targeted genome editing of an animal using site specific homologous integration. A composition comprising a single stranded oligonucleotide or double stranded nucleic acid molecule comprising a nucleic acid molecule of interest and sequences flanking a target locus cleavage site is injected into the zygote of an animal along with a nuclease and a guide nucleic acid molecule that targets the nuclease to a target locus. The composition is injected into the zygote after fertilization and prior to formation of a nucleus. The nucleic acid molecule of interest is recombined into the genome with high efficiency. The process allows for integration of nucleic acid molecules into the genome of animals in which the pronuclei cannot be visually observed during injection.

28 Claims, 7 Drawing Sheets

Specification includes a Sequence Listing.

Mouse zygote

Pig zygote

Crispr-Cas9&sgRNA+Loxp oligo (Zbed6)

*Blastocyst 1*

```
Zbed6 AGAAGGGTTTGCGAATTA----------------------------------AGGGGAAAAGGCGAC
1     AGAAGGGTTTGCGAATTCTACCGTTCGTATAGCATACATTATACGAAGTTATAGGGGAAAAGGCGAC
2     AGAAGGGTTTGCGAATTCTACCGTTCGTATAGCATACATTATACGAAGTTATAGGGGAAAAGGCGAC
3     AGAAGGGTTTGCGAATTCTACCGTTCGTATAGCATACATTATACGAAGTTATAGGGGAAAAGGCGAC
```

*Blastocyst 2*

```
Zbed6 AGAAGGGTTTGCGAATTA--------------------------------AGGGGAAAAGGCGAC
1     AGAAGGGTTTGCGAATTCTACCGTTCGTATGCATACATTATACGAAGTTAAGGGGAAAAGGCGGC
2     AGAAGGGTTTGCGAATTCTACCGTTCGTATGCATACATTATACGAAGTTAAGGGGAAAAGGCGGC
```

*Blastocyst 3*

```
Zbed6 AGAAGGGTTTGCGAATTA-------------------------------- AAGGGGAAAAGGCGAC
1     AGAAGGGTTTGCGAATTCTACCGTTCGTATGCATACATTATACGAAGTTAAGGGGAAAAGGCGAC
2     AGAAGGGTTTGCGAATTCTACCGTTCGTATGCATACATTATACGAAGTTAAGGGGAAAAGGCGAC
3     AGAAGGGTTTGCGAATTCTACCGTTCGTATGCATACATTATACGAAGTTAAGGGGAAAAGGCGAC
```

*Blastocyst 4*

```
Zbed6 AGAAGGGTTTGCGAATTA-------------------------------AGGGGAAAAGGCGAC
1     AGAAGGGTTTGCGAATCCTACCGTTCGTATGCATACATTATACGAAGTTAAGGGGAAAAGGCGAC
2     AGAAGGGTTTGCGAATCCTACCGTTCGTATGCATACATTATACGAAGTTAAGGGGAAAAGGCGAC
```

*Blastocyst 5*

```
Zbed6 AGAAGGGTTTGCGAATTA----------------------------------AGGGGAAAAGGCGAC
1     AGAAGGGTTTGCGAATTCTACCGTTCGTATAGCATACATTATACGAAGTTATAGGGGAAAAGGCGAC
2     AGAAGGGTTTGCGAATTCTACCGTTCGTATAGCATACATTATACGAAGTTATAGGGGAAAAGGCGAC
```

*FIG. 6*

PRNP with Loxp

LoxP Targeting

Zbed6 with loxp
(70% targeting)

PRNP with loxp
(100% targeting)

TARGETED GENOME EDITING IN ZYGOTES OF DOMESTIC LARGE ANIMALS

CROSS-REFERENCE TO RELATED APPLICATIONS

This application claims priority under 35 U.S.C. § 119 to provisional application Ser. No. 61/970,794 filed Mar. 26, 2014, herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Mar. 22, 2015, is named U of Maryland and is 16,384 bytes in size.

BACKGROUND OF THE INVENTION

Modification of animal genomes has multiple uses. Where a gene is modified, by, for example, silencing the gene, prohibiting the expression of protein, changing expression product or expression levels, the function of the gene or region of the gene becomes apparent. Changes to the gene may also result in modification to a more desired phenotype. Treatment of disease is also possible, where defective genes can be modified. Effective gene targeting of animals and in particular large domestic animals in which the pronuclei are difficult to visually identify in a fertilized zygote has numerous challenges preventing reliable delivery of targeting constructs in order to effectively target a specific region in such animal genome.

SUMMARY OF THE INVENTION

The present method allows for injection of nucleic acid molecules into zygotes of large animals followed by incorporation of the nucleic acid molecule into the nucleus of the cell, such that one need not visually identify the pronuclei of the zygote. The method provides for injecting nucleic acid molecules into the zygote after fertilization of an egg by sperm and prior to formation of a pronucleus. Methods in one embodiment employ homologous recombination with the resulting nucleus that is formed having the nucleic acid molecule of interest targeted. A double stranded break may be induced at the target locus in an embodiment of the invention. A nuclease and either single stranded oligonucleotides or a double stranded targeting vector is provided with heterologous nucleic acid molecules of interest and sequences having homology to sequences flanking the site of the double stranded break, which allows for homologous recombination at the site. In an embodiment, the flanking sequences may be 50 base pairs (bp) or more when using single stranded oligonucleotides, and may be 500 bp or more when using a double stranded targeting vector. The method may be used for modifying expression of sequences in the animal by, for example, inhibiting expression, deletion, replacement of alleles, or introducing into the animal genome a sequence, which in one embodiment expresses a unique protein.

BRIEF DESCRIPTION OF THE DRAWINGS

FIG. 6 shows sequencing of the recombined ZBED6 allele (the entire sequence shown is SEQ ID NO: 13) showing the EcoR1 site (underlined) and the LoxP (SEQ ID NO: 11) site in the inset.

DETAILED DESCRIPTION OF THE PREFERRED EMBODIMENTS

Figure 1:
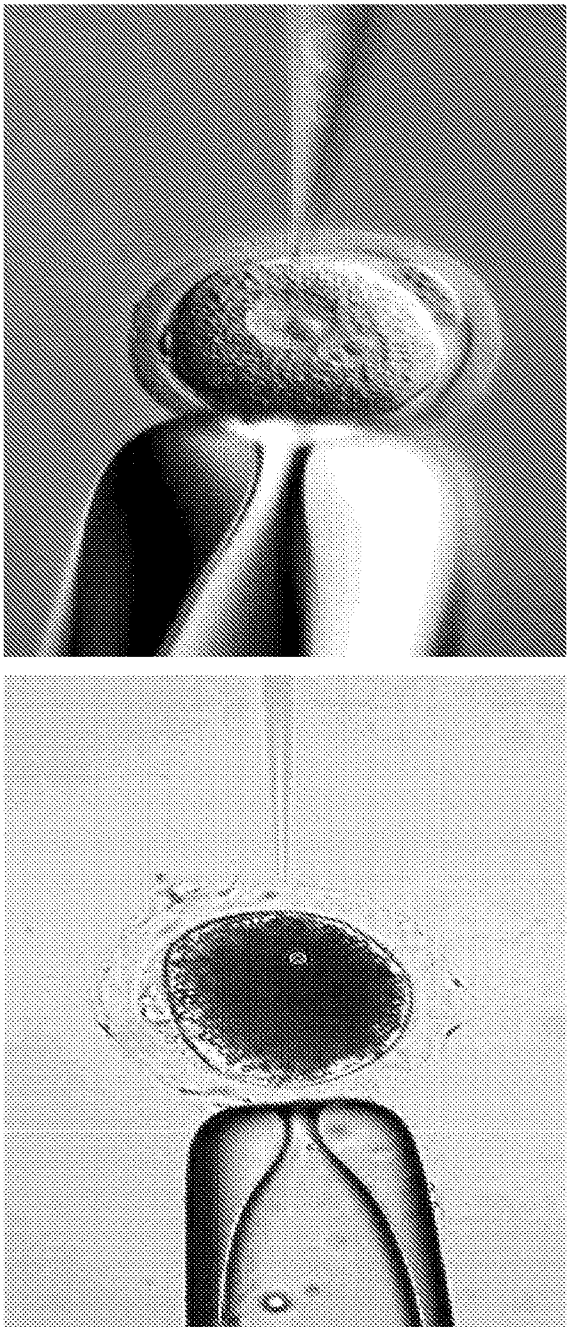
FIG. 1 is a photomicrograph of porcine and murine zygotes.

Transfer of genetic material into mammalian cells was first reported 50 years ago (Szybalska, E. et al. Genetics of human cell line. IV. DNA-mediated heritable transformation of a biochemical trait. *Proc Natl Acad Sci USA* 48, 2026-2034 (1962)) when cells were made resistant to hypoxanthine, aminopterin and thymidine (HAT) selection medium by calcium phosphate mediated transfection. The efficiency of exogenous transfer was further improved by injection of DNA directly into tissue culture cells with the aid of micropipettes mounted on micromanipulators. (Graessmann, et al. Retransformation of a simian virus 40 revertant cell line, which is resistant to viral and DNA infections, by microinjection of viral DNA. *J Virol* 32, 989-994 (1979);

Capecchi, et al. High efficiency transformation by direct microinjection of DNA into cultured mammalian cells. *Cell* 22, 479-488 (1980)). This served as a prelude for injection of transgenes into the pronucleus (PN) of mouse zygotes (Gordon, J et al. Genetic transformation of mouse embryos by microinjection of purified DNA. *Proc. Natl. Acad. Sci. USA* 77, 7380-7384 (1980)) and the production of the first transgenic mice. (Brinster, R. L. et al. Somatic expression of herpes thymidine kinase in mice following injection of a fusion gene into eggs. *Cell* 27, 223-231 (1981)). Soon after the first demonstrated success in generating transgenic mice by PN injection, similar procedures were used to generate growth hormone transgenic pigs. (Hammer, R. E. et al. Production of transgenic rabbits, sheep and pigs by microinjection. *Nature* 315, 680-683 (1985)). The PN injection procedure remains a widely used technique for making transgenic domestic large animals, such as pigs, cattle, sheep, goats, camelids, dogs, cats, etc., however, only 1% of injected zygotes produce stable transgenic founders. (Niemann, H. Transgenic pigs expressing plant genes. *Proc Natl Acad Sci USA* 101, 7211-7212 (2004); Prather, et al. Genetically modified pigs for medicine and agriculture. *Biotechnology & Genetic Engineering Reviews* 25, 245-265 (2008)). In addition to low efficiencies in generating founder animals, the technique is challenging in pig and other large animal models, where the embryo is murky and the pronucleus is difficult to localize for injecting large DNA constructs (FIG. 1).

Besides PN injection, other methods for generating transgenic animals have been attempted, which included sperm-mediated gene transfer, oocyte transduction, and transposons, with varying degree of success. (Park, et al. Role of stem cells in large animal genetic engineering in the TALENs-CRISPR era. *Reprod Fertil Dev* 26, 65-73 (2013)). Specifically in conjunction with the use of CRISPR/Cas system or other site specific nucleases, such DNA constructs can be targeted to a specific region of the gene, allowing for site-specific knockin of the candidate genes, modification of nucleotides or replacement of alleles. However, all the methods suffer from somewhat similar limitations, including (but not limited to): (1) random integration in the genome; (2) insertional mutagenesis; (3) positional silencing; (4) lack of control over the number of integrants and expression; (5) an inability to pre-screen for stable integrations before embryo transfer; and (6) the inability to delete endogenous genes (i.e. gene “knockout” or “KO”, where the gene expression is inactivated or inoperative). “Gene targeting”, whereby the intended gene sequences can be targeted for deletion, or exogenous DNA incorporated, offsets all the disadvantages described above.

Success in gene targeting can be attributed to the discovery that flanking homologous isogenic sequences combined with a positive and negative selection scheme facilitates the creation and identification of recombination events at the intended locus (Luciw, et al. Location and function of retroviral and SV40 sequences that enhance biochemical transformation after microinjection of DNA. *Cell* 33, 705-716 (1983); Kucherlapati, R. S. et al. Homologous recombination in monkey cells and human cell-free extracts. Cold Spring Harbor Symposia on Quantitative Biology 49, 191-197 (1984)). However, one of the major limitations of homologous recombination (HR)-based gene targeting for knocking out genes, introducing point mutations, or knocking-in genes is the poor efficiency of achieving correct recombination events, typically in the range of 1 in $10^6$-$10^7$ cells. In addition, these modifications are often monoallelic in nature, requiring a second round of targeting for bi-allelic (homozygous) modifications. In pigs and other livestock species that lack genuine embryonic stem cells (ESC), somatic cells, typically fetal fibroblasts are used for gene targeting, and the modified cells are used as donor cells in nuclear transfer or cloning to generate the genetically modified (GM) animals. The gene targeting efficiencies are relatively poor when using somatic cells as precursors, which is further compounded by the relatively early senescence of the fibroblasts precluding characterization of the desired knock in (KI) or other genetic alterations in the course of the experiment. With the long gestation length and maturation to reproduction age of pigs and other large animals, the generation of homozygous knockin (or “KI”, where a nucleic acid sequence is inserted at a particular locus) animals by nuclear transfer or cloning to produce recombinant pigs is both technically challenging and cost prohibitive.

An improved method is shown here of targeting genome editing in zygotes that allows for genome targeting in animals including animals having a zygote with optical density such that the pronuclei are obscured as a result of lipid granules in the cytoplasm interfering with visualization. This makes it difficult to visually identify the pronuclei of the zygote with the naked human eye and inject nucleic acid molecules into the nuclei. A pronucleus is the haploid nucleus of a sex cell, here the male and female pronuclei present following fertilization of the oocyte (egg) by the spermatatozoa (sperm). The membranes of the pronuclei dissolve and the chromosomes align, then becoming part of a single diploid nucleus and cell division occurs. One skilled in the art appreciates that it is possible to determine the time frame prior to formation of the pronuclei into nucleus. Using homologous recombination techniques, precise targeting of a nucleic acid molecule to a location of the genome is now possible using direct injection into such animal zygotic cells where the injection occurs after fertilization and prior to the pronuclei forming a nucleus. Using this method it has been found the nucleic acid molecule will be efficiently recombined into the nucleus. One embodiment provides for injection up to 18 to 24 hours after fertilization. In an embodiment the time frame is at up to five hours in one embodiment, and up to 12 hours in another embodiment. At embodiment provides injection occurs at three, four or five hours after fertilization. For about three to five hours after fertilization the cells are typically kept in a fertilization medium, and would be injected after removal from the medium. In a further embodiment injection occurs about up to 16 hours after fertilization, in an embodiment is three to four to five to six to seven to eight to nine to ten to twelve to thirteen to fourteen to fifteen hours after fertilization up to 16 hours, and in further embodiment is 8 to 12 hours after fertilization. This avoids the need to use fetal fibroblasts or a system of nuclear transfer or cloning. A nucleic acid sequence of interest is injected along with components which target the sequence to the desired target locus in the genome and provide for homologous recombination at the site. Such components in an embodiment include a nuclease for cleaving the target locus, along with a guide RNA that directs the nuclease to the targeted locus.

Any method which provides for targeting of the nucleic acid molecule of interest (NOI) to the target site of the target gene may be utilized in the method. The following is provided by way of example rather than limitation. A guide nucleic acid molecule is one that directs the nuclease to the specific cut site in the genome, whether via use of a binding domain, recognition domains, guide RNAs or other mechanisms. The guide nucleic acid molecule is introduced into the cell under conditions appropriate for operation of the guide nucleic acid molecule in directing cleavage to the target locus. A person of skill in the art will have available a number of methods that may be used, the most common utilizing a nuclease to cleave the target region of the gene, along with sequences which will recognize sequences at the target locus and direct cleavage to the locus. Any nuclease that can cleave the phosphodiester bond of a polynucleotide chain may be used in the methods described here. By way of example without limitation, available systems include those utilizing site specific nucleases (SSN) such as ZFNs (Zinc finger nuclease), (Whyte, J. J. et al. Gene targeting with zinc finger nucleases to produce cloned eGFP knockout pigs. *Mol Reprod Dev* 78, 2 (2011); Whyte, et al. Cell Biology Symposium: Zinc finger nucleases to create custom-designed modifications in the swine (*Sus scrofa*) genome. *J Anim Sci* 90, 1111-1117 (2012)); TALENs (Transcription activator-like effector nucleases) (see, Carlson, D. F. et al. Efficient TALEN-mediated gene knockout in livestock. *Proc Natl Acad Sci USA* 109, 17382-17387 (2012); Tan, W. et al. Efficient nonmeiotic allele introgression in livestock using custom endonucleases. *Proc Natl Acad Sci USA* 110, 16526-16531 (2013); Lillico, S. G. et al. Live pigs produced from genome edited zygotes. Scientific reports 3, 2847 (2013)), and the CRISPR (Clustered regularly interspaced short palindromic repeats)-associated (Cas) nuclease system (Hai, T., Teng, F., Guo, R., Li, W. & Zhou, Q. One-step generation of knockout pigs by zygote injection of CRISPR/Cas system. *Cell Res* 24, 372-375 (2014)) that have permitted editing of animal genomes such as pig genomes with relative ease. The use of recombinases such as FLP/FRT as described in U.S. Pat. No. 6,720,475, or CRE/LOX as described in U.S. Pat. No. 5,658,772, can be utilized to integrate a polynucleotide sequence into a specific chromosomal site. Meganucleases have been used for targeting donor polynucleotides into a specific chromosomal location as described in Puchta et al., *PNAS USA* 93 (1996) pp. 5055-5060. ZFNs work with proteins or domains of proteins binding to a binding domain having a stabilized structure as a result of use a zinc ion. TALENs utilize domains with repeats of amino acids which can specifically recognize a base pair in a DNA sequence. For a discussion of both systems see Voytas et al. U.S. Pat. No. 8,697,853, incorporated herein by reference in its entirety. These systems utilize enzymes prepared for each target sequence.

The CRISPR/Cas nuclease system has evolved in archaea and bacteria as a RNA based adaptive immunity system to detect and cleave invading viruses and plasmids. (Horvath, P. & Barrangou, R. CRISPR/Cas, the immune system of bacteria and archaea. *Science* 327, 167-170 (2010); Wiedenheft, et al. RNA-guided genetic silencing systems in bacteria and archaea. *Nature* 482, 331-338 (2012)). Unlike ZFNs and TALENs, which require assembly of DNA binding domain (DBD) to direct the nuclease to the target site, the CRISPR/Cas system utilizes RNA as a guide. The CRISPR locus is a distinct class of interspersed short sequence repeats (SSRs) recognized in bacterial genes. The repeats are short elements occurring in clusters that are regularly spaced by unique intervening sequences with a substantially constant length. They were observed as an immunity system in which nucleic acid molecules homologous to virus or plasmid sequences are integrated into the CRISPR loci. The foreign DNA or RNA is targeted and cleaved. The system has been adapted for targeted insertion of a nucleic acid molecule at a defined locus. In general, a CRISPR system is characterized by elements that promote the formation of a CRISPR complex at the site of a target sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. In the CRISPR system one enzyme, a CRISPR enzyme is used for targeting using short RNA molecules.

Two basic components are used with the system, a guide RNA and an endonuclease. The guide RNA is endogenous sequence specifying the target site and tracrRNA, needed to bind to the enzyme. The guide sequence provides target specificity and the tracrRNA provides scaffolding properties. These guide sequences are typically about 15 up to 20 to 25 base pairs (bp) that hybridize with the target site and direct binding of a CRISPR complex to a target sequence. A sequence encoding a CRISPR-associated enzyme may be provided on the same or different vectors. Non-limiting examples of Cas proteins include Cas1, Cas1B, Cas2. Cas3, Cas4, Cas5, Cash. Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In one embodiment the enzyme is a type II CRISPR system enzyme and is Cas9 or variants or modifications thereof. These enzymes are known; for example, the amino acid sequence of *S. pyogenes* Cas9 protein may be found in the SwissProt database under accession number Q99ZW2. The enzyme or Cas9 protein can be used as a nickase or nuclease and cleave one or two strands of DNA. Cas9 has two functional domains, RuvC and HNH and when both are used both strands are cleaved. Cas9 nuclease forms a ribonuclease complex with target CRISPR RNAs (crRNAs) and transactivating RNAs (tracrRNA), and uses the chimeric RNA to target the genomic sequence and induce DSB. The CRISPR/Cas nuclease and other SSN can introduce a targeted double strand break (DSB) in the genomic DNA, which in the presence of a single stranded (SS) DNA oligonucleotide or a double stranded (DS) targeting vector, result in homologous recombination (HR) based alteration of selected nucleotides or KI of transgenes respectively, into the target loci. In another embodiment a SS oligonucleotide having the nucleic acid molecule of interest may be used with Cas9 mRNA and sgRNA to target modification of a particular target gene region. In further embodiments the target gene is complementary to the gRNA sequence and will have a protospacer adjacent motif or PAM sequence. This aids in binding by Cas9. For a discussion of details of the CRISPR/Cas system see Cong et al., U.S. Pat. Nos. 8,932,814; 8,871,445 and 8,906,616, incorporated by reference herein in their entirety.

Breaks in the genome can be repaired by the non-homologous end joining DNA repair pathway (NHEJ) or by homology directed repair pathway (HDR). NHEJ can disrupt the gene, by causing frame shifts or premature stop codons to occur. HDR is an embodiment that provides for insertion of a nucleic acid molecule that avoids such issues. With a double strand break a DNA repair template is provided in which sequences are provided that have homology to and hybridize with genome sequences flanking the cleavage site (homology arm). In one embodiment the DNA template or flanking sequences are transfected into the cell with the CRISPR/Cas vector.

Even though HDR-based gene targeting events are extremely rare, the efficiencies can be improved by several orders of magnitude (>1000-fold) by introducing a DSB at the target locus (Moehle, E. A. et al. Targeted gene addition into a specified location in the human genome using designed zinc finger nucleases. *Proc Natl Acad Sci USA* 104, 3055-3060 (2007)). Following DSB, either a SS oligo, or a DS vector with homology to the ends flanking the DSB, can produce animals with targeted genomic alterations or transgene integrations (Cui, L et al. The permissive effect of zinc deficiency on uroguanylin and inducible nitric oxide synthase gene upregulation in rat intestine induced by interleukin 1alpha is rapidly reversed by zinc repletion. *The Journal of Nutrition* 133, 51-56 (2003); Meyer, M et al. Gene targeting by homologous recombination in mouse zygotes mediated by zinc-finger nucleases. *Proc Natl Acad Sci USA* 107, 15022-15026 (2010)).

In the inventors laboratory, CRISPR/Cas mediated HDR and editing of nucleotides and gene KI by injections directly into the porcine zygotes bypassing the need for nuclear transfer/cloning to generate genetically modified (GM) animals. The length of each homology arm will vary depending on the size of the modification to the genome. Here, the inventors have discovered far smaller homology arms may be utilized than previously employed when not using the present method. Previously the sequence homologous to the target gene flanking sequences were required to be of a size in the region of 6000 bp. However, here with use of a double stranded break and site specific nuclease systems, it is demonstrated the methods need less than 6000 bp homologous regions, and operate with only at least about 40 bp, at least about 50 bp and amounts in-between, or more upstream and about 40 bp, at least about 50 bp and amounts in-between, or more downstream sequences for use with single stranded oligo and about at least 300 bp, at least 500 bp up to 1000 bp and amounts in-between or more with a double stranded targeting vector. This provides for a much less laborious process in preparing such sequences, reducing the time for preparation of a target vector to one to two weeks or less instead of six months. These homologous arms are provided with the SS oligonucleotide or DS vector.

The present methods provide for expansion of use in gene editing to provide greater efficiencies, by 10%, 20%, 30%, 40%, 50%, 60%, 70%, 80%, 90%, up to 100% increase and amounts in-between in the number of recombination events obtained. The fold increase in events recovered is up to 1000 fold or more. This results in high efficiency and usefulness with large animal gene editing and use in many settings.

In referring to a target gene is meant to refer to any nucleic acid molecule within the animal genome desired to be modified as described or where it is desired to insert a nucleic acid molecule. The target polynucleotide can be a sequence coding a gene product (e.g., a protein) or a non-coding sequence (e.g., a regulatory polynucleotide or a junk DNA).

The process is useful with knockins and knockouts. One can upregulate gene transcription through insertion of a transcriptional activator, for example, or repress expression using transcriptional repressors. Without intending to be limiting, among the variety of utilities of gene editing include modifying (e.g., deleting, inserting, translocating, inactivating, activating, mutating) a target polynucleotide in a multiplicity of cell types. In some embodiments the polypeptide expressed may be modified. There are a broad spectrum of applications in, e.g., gene therapy, drug screening, disease diagnosis, prognosis, increasing or decreasing growth and body composition, and improving quality or composition of animal products. The methods are useful in any situation where modification of a disease gene is desired. Further examples include improved feed use and meat composition, enhanced reproductive performance, changing component content of animal products such as milk (such as lactose content), and, reduce or eliminate phenotypes such as boar taint phenotype. The process is useful with so-called knockins where a sequence is inserted in the genome or knockouts where gene expression is reduced or eliminated or interrupted. This allows for understanding and control of the gene and its' downstream impact.

The target nucleotide may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease gene or polynucleotide. A "disease" gene or polynucleotide includes any gene or polynucleotide associated with impacting disease in and animal and can include a gene or polynucleotide which is yielding transcription or translation products at an abnormal level or in an abnormal form in cells derived from a disease-affected tissues compared with tissues or cells of a non-disease control. A disease gene is any gene associated with an increase or decrease in the risk of having or developing a disease or recovery from disease. It may be a gene that becomes expressed at an abnormally high level; it may be a gene that becomes expressed at an abnormally low level, where the altered expression correlates with the occurrence and/or progression of the disease. A disease gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. A vast array of animal diseases may be treated, prevented or studied by use of the methods here with genes or proteins encoded associated with the disease. A few examples include the PRNP gene providing resistance to transmissible spongiform encephalopathies; upregulation of SOCS1, SOD2, RBP4, HLA-B, HLA-G, PPP2R1A and TAP1 gene or downregulation of IL18, TF, C4BPA, C1QA, C1QB and TYROBP genes of immune response genes in protection from PRRSV; KI decoys to combat zoonotic flu disease, eliminating negative phenotypes such as boar taint, and introgress agriculturally beneficial traits.

A still further example of potential uses provides for introduction into the animal cell of interfering nucleic acid molecules. For example, double-stranded RNA molecules (dsRNA) may be employed. In this process, in summary, RNA which is double stranded, in part, or completely, is produced based upon the sequence of the target nucleic acid molecule. Specifics of the means of producing the dsRNA may vary as one skilled in the art appreciates, and include, by way of example without intending to be limiting, the approach of Graham et al., U.S. Pat. No. 6,573,099 where two copies of a sequence corresponding to a target sequence is used, or that of Fire et al., U.S. Pat. No. 6,326,193 (both incorporated herein by reference), where the first strand is an RNA sequence corresponding to the target nucleic acid, and the second is one which is complementary to the target sequence, each of which are incorporated herein by reference in their entirety. These strands hybridize with each other to form the inhibiting dsRNA. The strand which corresponds to the target nucleic acid molecule can correspond to all or a portion thereof, as long as a dsRNA is formed. Where a strand is used which is the complement (antisense) of the target nucleic acid is used, it can be complementary to all or a portion of the target nucleic acid molecule, so long as the dsRNA formed interferes with the target nucleic acid molecule. The dsRNA triggers a response in which the RNAse III Dicer enzyme process dsRNA into small interfering RNAs (siRNA) of approximately 21-23 nucleotides, which are formed into a RNA-induced silencing complex RISC which destroys homologous mRNAs. (See, Hammond, S. M., et al., *Nature* (2000) 404:293-296). Generally, sequences of up to 10 nucleotides 20 nucleotides, 30 nucleotides, 40 nucleotides, 50 nucleotides, 100 nucleotides, 200 nucleotides, 300, 500, 550, 500, 550, or greater and any amount in-between may be used.

One skilled in the art appreciates there are many uses available and which will become available for the methods described here.

The methods may be used in any animal. They are most useful with animals having pronuclei following fertilization that is at least partially visually obscured, making injection into the pronuclei difficult. Such pronuclei cannot be visually observed by the unaided human eye, that is, with the human eye and where visualized with a microscope, unaided by contrast, or other process to allow visualization. Such animals include "large domestic animals" that is, pigs, cattle, horses, dogs, cats, and other ruminant animals such as sheep, goats, oxen, musk ox, llamas, alpacas, guanicos, deer, bison, antelopes, camels, and giraffes oxen, musk ox, llamas, alpacas, guanicos, deer, bison, antelopes, camels, and giraffes. Livestock animals are among those included in the animals for which the processes can be used. Besides, in other animal models in which the cytoplasm is clear such as primates, rabbits, minks and other models, the procedure is still an attractive option, as it allows for not having to guess when the pronuclei are being formed, and instead the material can be injected into the cytoplasm.

The methods are particularly useful with swine. Pig is an economically important agricultural animal. Additionally, pigs are coveted for their biomedical applications. Similar to humans and mouse, the pigs are mono-gastric, and as such are playing a dominant role in investigations of nutrient uptake, trafficking and metabolism. (Patterson, et al. The pig as an experimental model for elucidating the mechanisms governing dietary influence on mineral absorption. *Experimental biology and medicine* 233, 651-664 (2008)). Advances in the field of animal genome editing have included sequencing of pig genome. (Groenen, M. A. et al. Analyses of pig genomes provide insight into porcine demography and evolution. *Nature* 491, 393-398 (2012)). Taken together, depending on the biological question that needs to be addressed, a suitable pig model is available for investigation. However, until now there has been a lack of incentive for the use of pig as "preferred models", due to the GM technologies that lag behind the mouse models. The present methods address these shortcomings.

In recent years, there is an increasing consensus that the mouse, although still a powerful genetic model species, has limitations and cannot fulfill the full spectrum of biomedical demands to address preventative medicine (obesity, infertility, cardiovascular disorders), identification of new or improved diagnostics, and models of farm derived zoonotic diseases. As an alternative, large domesticated animals such as pig are gaining favor, because they are more similar anatomically, physiologically, and immunologically to humans, while maintaining the advantages of being a litter bearing species and a relatively long life span permitting long term investigations. Examples where the mouse model has not met expectations due to differences in anatomy or physiology include, cystic fibrosis, ocular and cardiac diseases. (Rogers, C. S. et al. Disruption of the CFTR gene produces a model of cystic fibrosis in newborn pigs. *Science* 321, 1837-1841 (2008); Welsh, M et al. Development of a porcine model of cystic fibrosis. *Transactions of the American Clinical and Climatological Association* 120, 149-162 (2009); Zhou, L. et al. Differentiation of induced pluripotent stem cells of swine into rod photoreceptors and their integration into the retina. *Stem Cells* 29, 972-980 (2011); Whyte, J. J. et al. Vascular endothelium-specific overexpression of human catalase in cloned pigs. *Transgenic Res* 20, 989-1001 (2011)). As almost all domestic pigs are crossbreeds, the resulting phenotype from these animal models is more reliable and applicable to the human diseases than inbred mouse strains. Likewise, the domestic pigs are better suited for zoonotic or infectious disease research, where they serve as reservoir or carriers of the disease, or are natural hosts to the pathogen. In addition to serving as models of human disease, the domestic pig is coveted for studies where the relatively long life span, close similarity in body size and physiology to humans offer an advantage. Briefly, pigs are preferred models for nutritional studies.

In referring to injection is meant any convenient method of inserting a device into the cell and passage of the nucleic acid molecules into the cell. By way of example without limitation, this can be accomplished with an injection pipette which may include a syringe holding the nucleic acid molecules. The pipette is inserted through the zona pellucida. Contrary to present techniques, one need not be able to visually observe the pronuceli in order to contact the injection device with the pronuclei. Instead, one need only introduce the nucleic acid molecules into the fertilized oocyte, without concern if the pronuclei are contacted, and introduction into the cytoplasm is sufficient. The injection occurs after fertilization and prior to the pronuclei forming a nucleus. Prior to fertilization, the female DNA will be at metaphase II stage and not have completed meiosis. The sperm stimulates meiosis and eventual formation of a nucleus. Here injection occurs before the nucleus forms. An embodiment provides the injection occurs up to 16 hours and, in an embodiment, 12 to 16 hours after fertilization, in another embodiment three, four, five or 6 to 12 hours after fertilization and in a further embodiment 16 hours after fertilization. As noted herein, one skilled in the art can determine when, in a particular animal, the nucleus will be formed and inject prior to that time. In pigs and cows for example, the time frame is 12 to 16 hours after fertilization. Without wishing to be bound by any theory it is believed this provides sufficient time to dissipate the molecules in the cytoplasm and for the nuclease recombination components to integrate the nucleic acid molecule into the eventual nucleus. Not only does this allow for introduction of nucleic acid molecules into large animals in which injection of the pronuclei was difficult, but also provides high event recovery, here, up to 100%, and avoids problems with production of a mosaic which can occur if recombination occurs after DNA replication.

As used herein, the terms nucleic acid or polynucleotide refer to deoxyribonucleotides or ribonucleotides and polymers thereof in either single- or double-stranded form unless indicated otherwise. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260: 2605-2608; Rossolini et al. (1994) *Mol. Cell. Probes* 8:91-98). The term nucleic acid is used interchangeably with gene, cDNA, and mRNA encoded by a gene.

A "polypeptide" refers generally to peptides and proteins. In certain embodiments the polypeptide may be at least two, three, four, five, six, seven, eight, nine or ten or more amino acids or more or any amount in-between. A peptide is generally considered to be more than fifty amino acids. The terms "fragment," "derivative" and "homologue" when referring to the polypeptides according to the present invention, means a polypeptide which retains essentially the same biological function or activity as said polypeptide. Such fragments, derivatives and homologues can be chosen based on the ability to retain one or more of the biological activities of the polypeptide. The polypeptides may be recombinant polypeptides, natural polypeptides or synthetic polypeptides.

Thus when referring to a nucleic acid molecule of interest (NOI) is meant a nucleic acid molecule which is desired to be introduced into the animal cell nucleus. An NOI, then, by way of example without limitation, may be the target gene and may be modified; RNA; interfering RNA; a nucleic acid molecule that can have various impact on the target gene or another gene, as discussed herein; a nucleic acid molecule newly inserted into the genome and that may produce an additional polypeptide within the genome, or a combination of any of these. Any nucleic acid molecule desired to be introduced into the animal cell genome can be the NOI.

"Codon optimization" can be used to optimize sequences for expression in an animal and is defined as modifying a nucleic acid sequence for enhanced expression in the cells of the animal of interest, e.g. swine, by replacing at least one, more than one, or a significant number, of codons of the native sequence with codons that are more frequently or most frequently used in the genes of that animal. Various species exhibit particular bias for certain codons of a particular amino acid. Cas9 can be one of the sequences codon optimized for improved expression.

In one aspect, polynucleotides comprising nucleic acid fragments of codon-optimized coding regions which may produce RNA, encode polypeptides, or fragments, variants, or derivatives thereof, with the codon usage adapted for optimized expression in the cells of a given animal. These polynucleotides are prepared by incorporating codons preferred for use in the genes of the host of interest into the DNA sequence.

A "heterologous" nucleic acid molecule is any which is not naturally found next to the adjacent nucleic acid molecule. A heterologous polynucleotide or a heterologous nucleic acid or an exogenous DNA segment refers to a polynucleotide, nucleic acid or DNA segment that originates from a source foreign to the particular host cell, or, if from the same source, is modified from its original form in composition and/or genomic locus by human intervention. A heterologous gene in a host cell includes a gene that is endogenous to the particular host cell, but has been modified or introduced into the host. Thus, the terms refer to a nucleic acid molecule which is foreign or heterologous to the cell, or homologous to the cell but in a position within the host cell nucleic acid in which the element is not ordinarily found.

A nucleic acid may then be introduced into an animal host cell through the use of a vector, plasmid or construct and the like. A "vector" is any means for the transfer of a nucleic acid into a host cell. Vectors can be single stranded, double stranded or partially double stranded, may have free ends or no free ends, may be DNA, RNA or both. A variety of polynucleotides are known to be useful as vectors. A plasmid is a circular double stranded DNA loop. Referring to one or more expression vectors is meant to refer to one or more vectors comprising necessary regulatory elements for proper expression of the operably linked nucleic acid molecules. A vector may be a replicon to which another DNA segment may be attached so as to bring about the replication of the attached segment. A replicon is any genetic element (e.g., plasmid, phage, cosmid, chromosome, virus) that functions as an autonomous unit of DNA or RNA replication in vivo, i.e., capable of replication under its own control. The term "vector" includes both viral and nonviral means for introducing the nucleic acid into a cell in vitro, ex vivo or in vivo. Viral vectors include but are not limited to adeno-associated viruses, lentiviruses, alphavirus, retrovirus, pox, baculovirus, vaccinia, herpes simplex, Epstein-Ban, rabies virus, and vesicular stomatitis virus. Non-viral vectors include, but are not limited to plasmids, liposomes, electrically charged lipids (cytofectins), DNA- or RNA protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.). Transformed cells can be selected, for example, by resistance to antibiotics conferred by genes contained on the plasmids, such as the amp, kan, gpt, neo and hyg genes. The techniques employed to insert such a sequence into the viral vector and make ether alterations in the viral DNA, e.g., to insert linker sequences and the like, are known to one of skill in the art. (See, e.g., Sambrook et al., 2001. *Molecular Cloning: A Laboratory Manual,* $3^{rd}$ Edition. Cold Spring Harbor Laboratory Press, Plainview, N.Y.). A "cassette" refers to a segment of DNA that can be inserted into a vector at specific restriction sites. The segment of DNA encodes a polypeptide of interest or produces RNA, and the cassette and restriction sites are designed to ensure insertion of the cassette in the proper reading frame for transcription and translation.

The nucleic acid molecule may be operably linked to a suitable promoter at the 5' end and a termination signal and poly(A) signal at the 3' end. As used herein, the term "operably linked" means that the nucleic acid molecule containing an expression control sequence, e.g., transcription promoter and termination sequences, are situated in a vector or cell such that expression of the polypeptide or RNA produced by the nucleic acid molecule is regulated by the expression control sequence. Methods for cloning and operably linking such sequences are well known in the art. Promoters may direct constitutive expression or tissue preferred expression. Tissue-preferred (sometimes called tissue-specific) promoters can be used to target enhanced transcription and/or expression within a particular cell or tissue. Such promoters express at a higher level in the particular cell region or tissue than in other parts of the cell or tissue and may express primarily in the cell region or tissue. Examples include promoters that secrete to the cell wall, retain expression in the endoplasmic reticulum, or target vacuoles or other cell organelles. Other may direct expression primarily to muscle, neuron, bone, skin, blood or specific organs or cell types. Such promoters may also direct expression in a temporal manner, expressing at a particular stage of development or cycle of the cell. The promoter(s) utilized in one example may be polymerase (pol) I, pol II or pol III promoters. Examples of pol I promoters include the chicken RNA pol I promoter. Examples of pol II promoters include but are not limited to the cytomegalovirus immediate-early (CMV) promoter, the Rous sarcoma virus long terminal repeat (RSV-LTR) promoter, and the simian virus 40 (SV40) immediate-early promoter. Examples of pol III promoters includes U6 and H1 promoters. Inducible promoters may be used such as the metallothionein promoter. Other examples of promoters include, T7 phage promoter, T3 phage promoter, beta-galactosidase promoter, and the Sp6 phage promoter. An example of a DNA having a termination and poly(A) signal is the SV40 late poly(A) region. The use of these commercially available expression vectors and systems are well known in the art. The vector may contain multiple copies of a nucleic acid molecule of interest or a combination of nucleic acid molecules; also multiple vectors may be introduced simultaneously or sequentially into the cell.

Other components may be included in the vector or in vectors also introduced into the cells, such as polyadenylation sequences, enhancers, signal peptides, inducible elements, introns, translation control sequences or the like. As noted above, selectable markers allowing survival of cells with the vector or other identification of cells having the vector may be used.

A nucleic acid molecule is introduced into a cell when it is inserted in the cell. A cell has been "transfected" by exogenous or heterologous DNA or RNA when such DNA or RNA has been introduced inside the cell. When referring to integration of a nucleic acid molecule into a cell is meant that the molecule has recombined and become part of the genome.

The presence of the nucleic acid molecule of interest may be determined by any convenient technique, such as identifying the presence of a marker gene; detecting the presence of the inserted sequence via PCR or the like; detecting expression product from animal cells, tissue or fluids; Northern or Western blot analysis; or any other readily available method.

All references cited herein are incorporated herein by reference. The examples presented are provided by way of illustration and not meant to limit the scope of the invention.

EXAMPLES

CRISPR Mediated Gene Knock-ins:

In the inventors' laboratory, major prion protein (PRNP) has been used as a so-called "safe harbor" locus for targeted KI of transgenes. In mouse, transgenes are typically knocked into the Rosa26 locus, which is ubiquitously expressed in all target tissues, and has been shown not to be vital for the survival of offspring if deleted. (SEQ ID NO: 1 is the PRNP protein Gene ID: 494014) Therefore, Rosa26 has been the preferred site for inserting transgenes to prevent both: a) inadvertent silencing of the transgene; and b) insertional mutagenesis caused by random insertion of a transgene into an off-target site in the genome. In mouse, besides Rosa26, PRNP is another ubiquitously expressed gene, and is not required for viability, thereby qualifying as a safe harbor locus. Such a safe harbor gene is one that meets the criteria of having no known adverse effect on the cell by introduction of the vector or nucleic acid molecule into the site and has transcriptional competence across cell types. Besides mice, PRNP−/− cattle are also healthy. (Richt, J. A. et al. Production of cattle lacking prion protein. *Nat Biotechnol* 25, 132-138 (2007)). Any safe harbor gene may be utilized as desired for knockin of a nucleic acid molecule.

In pigs, and other large animals, the Rosa26 locus has not been characterized adequately. Hence, PRNP was selected as a safe harbor locus for targeted KO and KI of transgenes and establishing recombinant pigs. The results are discussed below.

A) Assembly of Targeting Vector:

A gene targeting vector was generated consisting of 500 bp upper arm and 1000 bp lower arm homologous to the Cas9 cut site (SEQ ID NO: 2 and 3 respectively) bordering exon-3 of PRNP gene. Using primers bearing unique restriction sequences AscI and XhoI, 1000 bp of sequence of upper arm was cloned into the corresponding sequences in the GFP (green fluorescent protein; see SEQ ID NO: 4 and GenBank U73901) expressing piggyBac vector. (SEQ ID NO: 5, 6,) Likewise, using primers consisting of BsiWI and MluI, 1000 bp of sequence downstream of the cut site were amplified and cloned into the same GFP piggyBac vector. (SEQ ID NO: 7, 8. The final targeting vector is generated by digesting the vector with AscI and HpaI and the linearized vector without prokaryotic sequences is injected into the embryos.

Figure 2A:
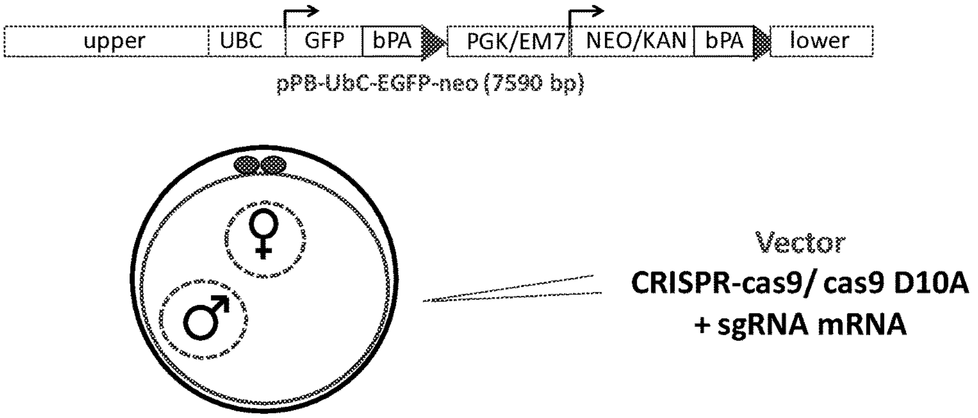
FIG. 2 shows CRISPR-mediated knockin of GFP transgene into the PRNP locus. A) is a schematic drawing of the targeting vector showing targeting arms homologous to endogenous PRNP locus. The term "upper" refers to the 500 bp of the targeted PRNP locus upstream of the cleavage site and "lower" refers to the 1000 bp of the downstream flanking sequence. UBC refers to (human ubiquitin C promoter), GFP refers to green fluorescent protein; bPA (bovine poly adenlyation transcription terminator sequence); PGK/EM7—is a hybrid eukaryotic (phosphoglycero kinase) and prokaryotic (EM7, a synthetic bacterial promoter derived from the T7 promoter that enables the constitutive expression of the antibiotic resistance gene in *E. coli* patents/U.S. Pat. No. 7,244,609) RNA polymerase II promoter sequences driving the expression of Neo/kan which are neomycin (or G418 for eukaryotic) and kanamycin resistance (for prokaryotic) selectable markers. The linearized targeting vector alongside, Cas9 mRNA and single guide (sgRNA) targeting PRNP are injected into the porcine zygotes. B) is a schematic showing an embodiment of the process. Cas9 induces double strand break in 3rd exon of PRNP. The broken DNA is then repaired with the targeting vector, resulted in the targeted allele.
Figure 2B:
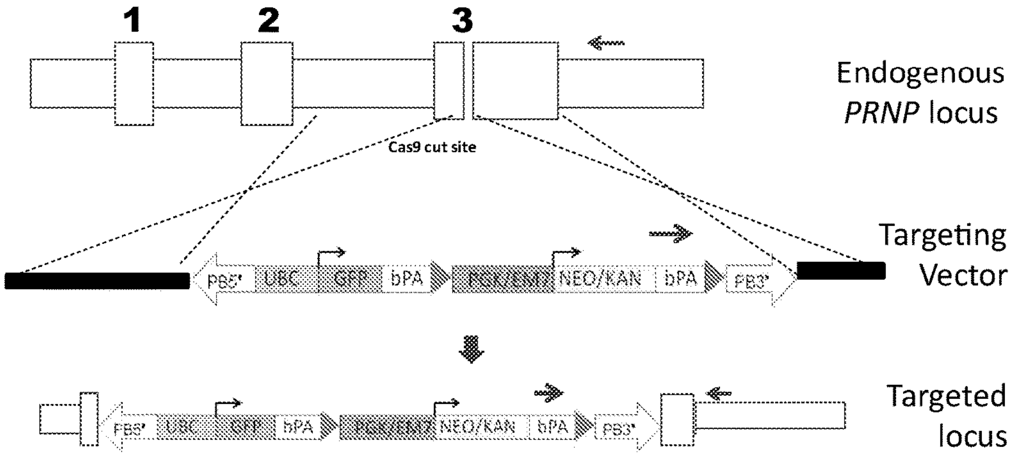

B) CRISPR Mediated Targeted Gene Knock-in in Porcine Embryos:

We investigated whether the gene targeting can be achieved by direct injections into the embryos thereby avoiding the need for targeting in an intermediate cell type and generating GM animals by cloning experiments. As noted in FIGS. 2*a* and 2B, by coinjection of targeting vector and CRISPRs (for generating DSB), we have demonstrated successful KI of GFP transgene into PRNP locus in embryos. In FIG. 2, UBC refers to (human ubiquitin C promoter), GFP refers to green fluorescent protein; bPA (bovine poly adenylation transcription terminator sequence); PGK/EM7—is a hybrid eukaryotic (phosphoglycero kinase) and prokaryotic (EM7, a synthetic bacterial promoter derived from the T7 promoter that enables the constitutive expression of the antibiotic resistance gene in *E. coli* patents/U.S. Pat. No. 7,244,609) RNA polymerase II promoter sequences driving the expression of Neo/kan which are neomycin (or G418 for eukaryotic) and kanamycin resistance (for prokaryotic) selectable markers. In the figure "Upper" refers to the upper 500 bp homologous sequences flanking the Cas9 cut site, and the "lower" refers to 1000 bp downstream sequences flanking the cleavage site.

Briefly, maturing oocytes from sows were purchased from ART Inc. (Madison, Wis.) and shipped to the lab overnight in their commercial maturation medium #1. Twenty-four hours after being placed in the maturation medium #1 (provided by ART), 50 to 75 cumulus-oocyte complexes (COCs) were placed in 500 μl of tissue culture medium 199 (TCM 199) containing 0.14% PVA, 10 ng/ml epidermal growth factor, 0.57 mM cysteine, 0.5 IU/ml porcine FSH, and 0.5 IU/ml ovine LH and cultured for an additional 20 hours at 38.5° C. and 5% CO2 in air, 100% humidity. (Abeydeera, L et al. Maturation in vitro of pig oocytes in protein-free culture media: fertilization and subsequent embryo development in vitro. *Biol Reprod* 58, 1316-1320 (1998)). COCs were vortexed in 0.1% hyaluronidase in HEPES-buffered medium containing 0.01% PVA for 4 minutes to remove the cumulus cells following maturation. Groups of 30-35 mature, denuded oocytes were placed in 100 μl of a modified Tris-buffered medium (mTBM) and fertilized according to established protocol (Abeydeera, L. R. & Day, B. N. Fertilization and subsequent development in vitro of pig ooytes inseminated in a modified tris-buffered medium with frozen-thawed ejaculated spermatozoa. *Biol*

Figure 3A:
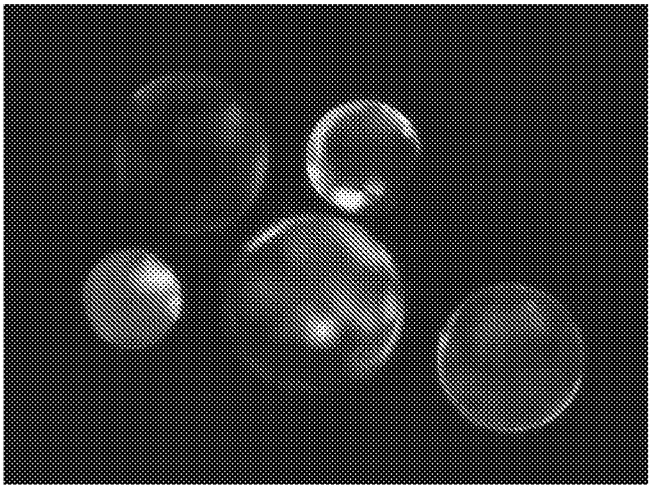
FIGS. 3 A and B are photos showing representative embryos that have developed to the blastocyst stage show expression of GFP, with A) showing the embryo under green fluorescent microscope and B) showing bright field microscope view.
Figure 3B:
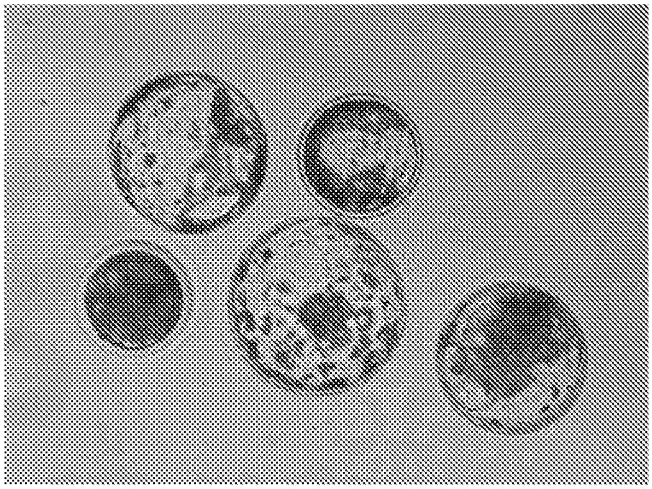

*Reprod* 57, 729-734 (1997)) using fresh extended boar semen. 1-2 ml of extended semen was mixed with Dulbecco's Phosphate Buffered Saline (DPBS) containing 1 mg/ml BSA to a final volume of 10 ml and centrifuged at 1000×g, 25° C. for four minutes; spermatozoa were washed in DPBS a total of three times. After the final wash, spermatozoa were resuspended in mTBM medium and added to oocytes at a final concentration of $5\times10^5$ spermatozoa/ml, and co-incubated for 5 hours at 38.5° C. and 5% $CO_2$. Five hours following fertilization, the presumptive zygotes were injected with 100 ng/ul of Cas9 mRNA alongside 50 ng/ul sgRNA targeting PRNP, and 2 ng/ul of linearized targeting vector using Eppendorf Transjector. Approximately, 50 nl of the mixture is injected into the porcine zygotes, and cultured in porcine in vitro culture PZM3 medium (Yoshioka, K et al. Birth of piglets derived from porcine zygotes cultured in a chemically defined medium. *Biol Reprod* 66, 112-119 (2002)) for 6 additional days. The injected embryos, which have now grown to blastocyst stage were screened for the expression of inserted GFP cassette. In FIGS. 3A and 3B, expression of GFP was apparent in the expanded blastocysts at day 6 of in vitro culture.

Figure 4:
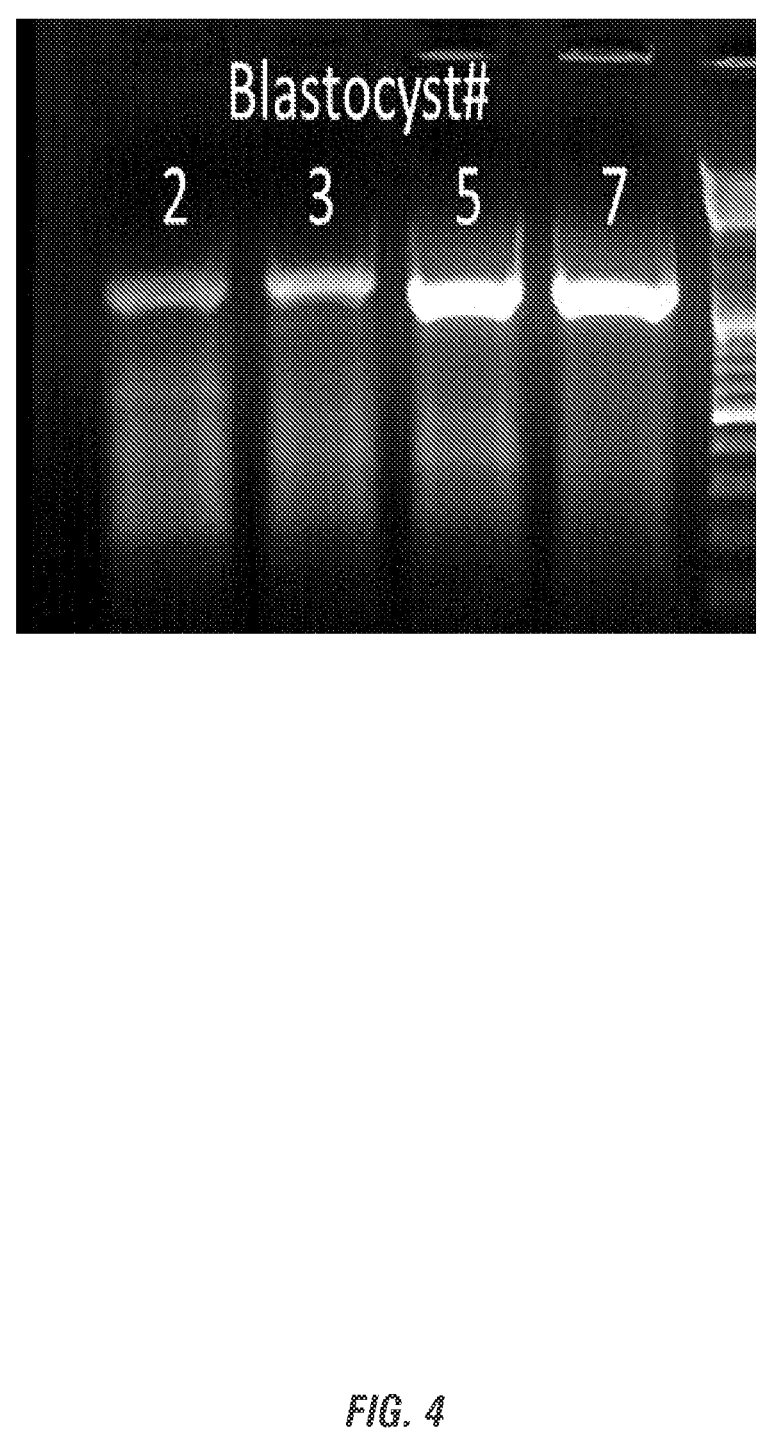
FIG. 4 is a gel where use of primers, one within the targeting vector and another outside of the homologous region, shows specific band of right size confirming targeting to the intended locus.

Targeted integration of GFP was also confirmed by PCR amplification of blastocyst DNA using primers both within and outside the targeting vector (FIG. 4). (SEQ ID NO: 9, 10) A final confirmation was obtained by sequencing of the PCR amplicon. We have performed transfers of these GFP KI embryos to recipient sows and the animals are pregnant at day 60 of gestation, and will likely give rise to the birth of live animals.

Single Stranded Oligo Mediated Genome Editing in Embryos:

With the sequencing of animal genomes it is now possible to identify quantitative trait loci (QTL) and in some cases quantitative trait nucleotides (QTN) that can influence the phenotype in question. It is imperative that these QTL and QTNs be tested. The ability to specifically alter nucleotides to accurately reflect superior or disease genotypes will be a powerful approach for improving animal agriculture and for generating disease models respectively. We have investigated if it will be possible to alter nucleotides to obtain desired phenotypes. This approach has the most direct applicability to animal agriculture where the negative traits such as boar taint, horned phenotype, disease susceptibility, and other parameters be altered with pinpoint accuracy to benefit the animals.

Figure 5A:
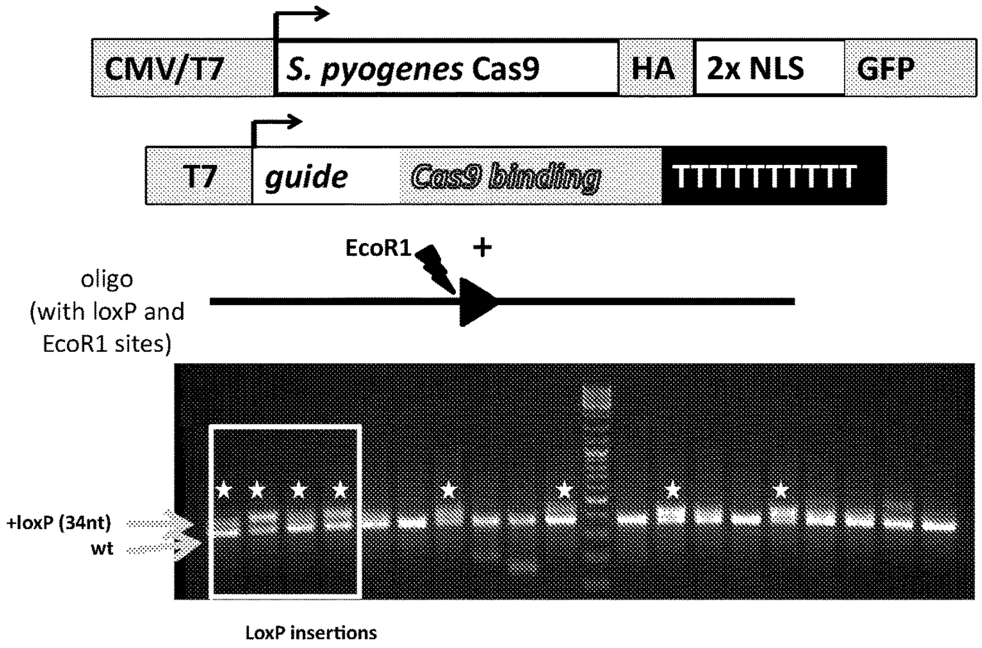
FIGS. 5A and B show CRISPR mediated homology directed repair and editing of porcine genomes using a single stranded oligonucleotide incorporation into the zygote. A) is a schematic of Cas9 vector, sgRNA targeting ZBED6 locus and a single stranded oligo containing a LoxP site and a EcoR1 restriction enzyme site injected into porcine zygotes. CMV and T7 refer to the promoters HA is HA tag, NLS is nuclear localization signal. B) is a gel showing the PCR amplicon contains the recombined EcoRI site, which can be digested to produce two fragments, confirming the recombination of a functional EcoR1 enzyme site.
Figure 5B:
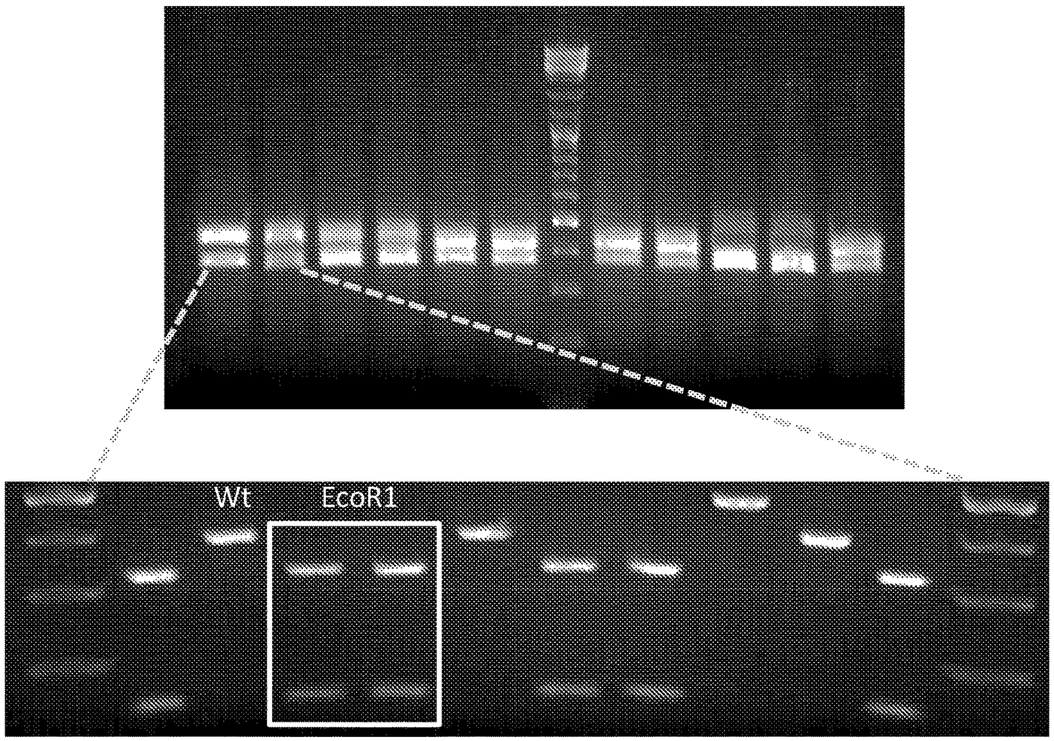
Figure 7A:
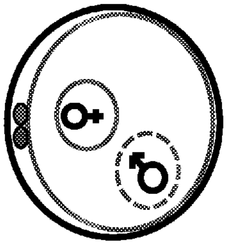
FIG. 7 shows A) a schematic of the pronuclei with loxP targeting; and two gels, B) a gel showing ZBED6 with loxP targeting and C) PRNP with loxP targeting.
Figure 7B:
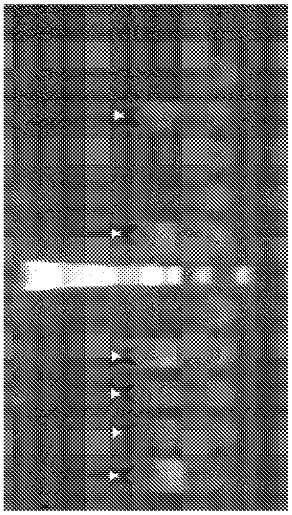
Figure 7C:
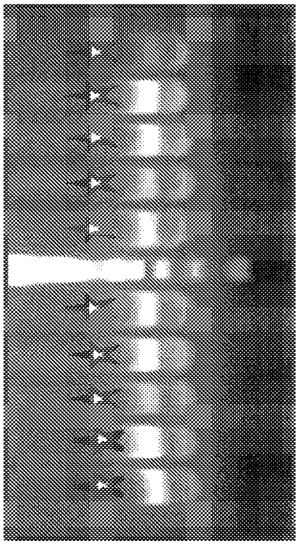

We have tested if specific loci can be targeted for introducing nucleotides by using single stranded oligo bearing the desired nucleotide modifications. In this case, we have investigated if we can target the PRNP loci to modify one of the existing nucleotides to generate a novel EcoR1 restriction enzyme (FIG. 5A). The promoters used were CMV and T7, HA refers to _HA tag, NLS is the nuclear localization signal which may be used to facilitate nuclear localization. In addition, for ease of analysis, a 34 nucleotide LoxP site (SEQ ID NO: 11 has been engineered on the oligo (FIG. 5A). As shown in FIG. 5B, we were able to alter a candidate ZBED6 locus by injecting the LoxP and EcoR1 restriction enzyme bearing oligo, along with Cas9 mRNA and sgRNA targeting ZBED6. (SEQ ID NO: 12). ZBED6 is a zinc finger protein that regulates expression of the insulin-like growth factor 2 gene in pigs. See Markljung et al., "ZBED6, a novel transcription factor derived from a domesticated DNA transposon regulates IGF2 expression and muscle growth. *PLoS Biol.* 7(12) e1000256. As mentioned above, the engineered ZBED6 locus could be visualized by a 34 nucleotide increase in the length of the PCR product, which was then verified by EcoR1 digestion. A final confirmation was evident from the sequencing of the targeted loci where the restriction site is shown as underlined (FIG. 6). We were able to repeat the results with PRNP (See FIG. 7. Cas9 was introduced at 100 ng/ul; sgRNA at 50 ng/ul and LoxP oligo at 2 ng/ul)

We have established a very efficient way for generating transgenic and/or edited animals, by eliminating intermediate steps and performing gene targeting directly in the embryos. The advantages with our approach are two-fold, one in generating targeting vectors and second in delivery of constructs. In terms of the targeting vector, a principle advantage is the less stringent requirement for lengthy homology arms in the targeting construct. In our experiments, gene targeting could be achieved with as small 300, up to 500, up to 1000 bp of homology on each targeting arm, a DNA fragment that is readily obtained by PCR of genomic DNA or can be synthesized as a G-block and obtained from IDT Inc. (FIG. 2A). This is in stark contrast to at least 6 kb of homology required for gene targeting in porcine fetal fibroblasts (PFF). In terms of delivery of the DNA constructs, we have identified a window of time post fertilization, where DNA and the CRISPR/Cas can be injected into the cytoplasm of the primitive pig zygote that allows the DNA to become packaged in the pronucleus when the nuclear envelopes are formed, thereby allowing for homologous recombination mediated gene targeting in the embryos. This strategy eliminates another major bottleneck in generating transgenic animals in pigs where locating pronucleus in the zygote for injecting transgenes has been a limiting factor. Additionally, the efficiencies of gene targeting were 80 to 100% with all of the blastocysts screened, showing accurate targeting of a KI construct in embryos. A final advantage is the ability to edit only few nucleotides precisely in the embryos, which have the ability to alter phenotype for agricultural applications, and for generating biomedical models. In summary, we have developed technologies to usher large animal biotechnology into the genomics era.

LIST OF SEQUENCES

SEQ ID NO: 1 the PRNP protein
NCBI Reference Sequence: NC_010459.4

```
ACGTACGCGGCCAAAAGAGTCTCAACTCCCTCCCA

GAGACTCAGATTTCCGACCAGCTTGGCAGATCCCG

GGCGCCGGAGCGCCAGAGCGCGCGCGCGCCGCC

GCCGCCTCCCTTCCCCGCCCGCGCGCCTCGCCACC

CCTCGGCGCCAGACACTGACAGCCCCGGAGCTGCG

AGCGTCTTCTGTTCCAGCGGTGGCAGGTAAACAGC

CGGGTCGCCCCGAGAACTGGGGGTGCCAAGGTCGG

GAGTCAGAACCCCCCGCCTTGGAGCTTAGGCGCAA

GGGTGAGCGGCCCACTTGGGGCGCTAGGGAAACCT

TGACAGAGAGGGGGGCGGGGGACTTCCGGCGGGCG

GGGGGCGCGACAGGCCTGCCCCCGCTTGTTCGTCG

GCTTAACATTGGCCCCGCTCACATTTGCTTTCCAG

GTGGGGTGAGGGCCCTTTACTCGGAATGGGGCTTG
```

-continued

GTGGGGGAAGGGGGTGCCTGGGGCTGGCCGCGACC
CCTGGGCAGGGAGGCGGATGGTGGCGGGGAGTCTA
GCCCTCTCCCACGCGCGTCCGCGGCTGGCGGAGGA
TGGGAGAGGCGCGCCGGCACCGGGGCCGCAGGGCC
GGGAACTCAAGGAGGGTCGCCCACGGCCTCCGCTG
AGGCGCTCGGAGGAGAACCAGGGAGAGGGGCCGGC
GTGCGGCTCTCCCGAGGCCCCAGGGGCACGTGGGG
TGGGGATGATGGCCCCGNNNNNNNNNNNNNNNNNN
NNNNNNNNNNNNNNNNNNNNNNNNNNNNNNNNNNN
NNNNNNNNNNNNNNNNNNNNNNNNNNNNNNNNNNN
NNNNNNNNNNNNAGCCCCAAGGGGCCCGTTGGGGG
GGGGTGATGGCCCAGGCCCCGGCGGGAGGGGCCCT
TGCCGCCGCCACCATGGAGCTCCTCCGGAGAGACG
GCCCACCTGCCATCCACGCGGCCCGGGGGTGCTGG
GGAGGCCGCAGCGGGGTGGGCCTCCTGCATCCCTG
GGGATGGAGACCGGGCACGTGGTCCGACCTTCGGG
CCTCGGCGGGCGGAGTCTCGGGCGGCCCCACCCTC
ACTGTCGGCCGAGACGTCCAGGTCCCTGGGGGCCG
AGTGTCCGGAGAGCCCAGGTGCTTTGCTTTTCACT
GTCTCCACTGCCCCTCCCCGAAGGGAACTGGGCGG
TCAGAGGCTCCTCTCAAGGGGATCAGGGCCGGACA
GCTCTCCTCCTGATCCACTTGTGTGGGCTGCCCTT
TCAGGCTTGATTGTAAACAACGAGGAGAAGTCCAT
TTTTACTGTCCCTTTTCATTTTTTTCCCTTTTCTA
AATTTGTAGCAACCATGGCAAATCAGTTTTTAAAA
TCATAACCCACAGCCATCAATCCACCCTTACCATC
TCAAAGCCACTGCTTTCTGTTTTTCAGTTTTCTGT
CTCCAGATTCGTACATAACGCAAAGAAATTTCAAC
TGCCCTGATTATGATTATCCTCCTCTAATGGCCGA
GTTATTTTCTTCTGCTTAAAGCGTCGCAGTTTAAT
AAGCAGTTCCCCGAATGCTGAACATTTGAAATGTT
TCGTTTTTTCTTGCAAAAAAACCTTCCAGGTATAA
CAGTATTAAAGAAAGAATAGGAATAGGAGTTCCCT
GGTGGCCTGGTGGTTAAGGATCCCATATTGTCGCT
GCTGTGGCTAGAGTTCCATCCCTGGCCCGGAAACT
TCTGTATACCTCAGGCAAGCCAACAAAAAGAAAAA
AAGAAGGGAAGAAAAGAAAAAAAATAGTAACAGAAA
ATTGAATTAATGTCAACCCCTGGAATTAACAACTA
TCTCAGATTTGAGGAAGAAAAAAAAAAAAAAAATC
AACAGTTTTACCTGCAGTAAACACTGAGGCGCTCT

-continued

TACAATGAAAAAGAACTAACCGGAAAGGGAAAGAA
AGCAGAGCTAGGATGTGATTTGTATATGATTTGTA
TCTGACACAAAATTTTCATAGTTATGAAAGGAAAA
TATGAAAATTATAATAAATGATGAATCAATTATAG
AATAAAATGTAAATTAAAGCACTCTGGATTATCAT
TTTACAATTACTAACAAATACAACAACAGTAATAG
TAACAGCAACCACTGTTGGAAGATTGCCTAGAAAT
TTTCACATTCAGTTATTTTGAGAGGTGGCAGGACT
TTGGGGTTAGAAGAATGGCTCTGCACCTAATTTCA
TAGCATGGAATGGGTTACCTAATTTCCTCATCCTC
CTTTTGTGCATTCATAAAATAGAGGAAATTATACC
TACTTCAGGAAATTGCTAAGATTAACCATCTATGT
AAAACTGACCTTTGGTATGTAATCCTTTTTCTATT
CTTGGGCACACTGCACTGGGGACATTGTGAATTTA
CTGTAAAGCAATTTGGTAATGCATTAGGCCATGAC
CCAGAATTTACCTGCAATGGAAGAAACAACAAGAA
AAAAAAGGGGGGGAAAAAAAAGCCATATGCAGTCA
CAGAATTCAGAATGATCTAAAATTAGACCCAACGG
AAAAACAACCTAAATGTATAACAGCAGGGCAGCAG
CTGAGGAAATCATGGCTCTTTAACTGAAAGAAACA
TTATGTAACTATCAAAAGTCGGTGGTACATGAGAA
AAAACTGATAAATCAGTGTAGATTACATTACCAAA
CTGTATCTACTTACTCAGTGAATGCATATGTGGAA
AATCTGAAAGGAAAAGCATACAAAGGAATTGAATA
GAATTAAAATGAAGTTAGAAATTATGGGTCAGTTT
AATTTTCTTTTTTATTTATATACTGCTTTTCTAAG
TAACGAAATTTTTAAGATAATTATTCATCGTTCTC
AATTTTTGTAATGAAATGGAGCCATAGTTTTCTGT
ATGTGGGAGAGGGAGAGCTCAGTGTCATGTTAGCT
GACTTCATTTCTTCAGATATTGTCTCTTTTTTTTT
CTCGTGTAGATGGATTAGGGGGTTAGTAATGTATA
TATTAGGATCCTTCTTTAAGGAATAGNNTCTAAAA
ATTATTATCAATTCTAGNTTTTTCTTTTTTTGGTG
TTTCTAAGGACCCTGAATATATTTGAAAACTGAAC
AGTTTCAGCTAAGCCGAAGCATTCTGTCTTCCCCA
GAACACAAATCCAGCCTCGCTGAGCCATTACAGAT
GTACATACTGCAGAGTCCCTTTGATCTCGTGATGG
CTCAGAGTCCCTATCTGTCACAGAAAAGAAGGGCC
TAGAAAGGCTATGATGACAGTCCTTGCTCTGAGGC
AACTTAGGGTTATATGTGTAACCCACACCTCTTAA
ATCATCCTTTCTTGTAAAATCATTTTGATTTTGCA

-continued

GGCAAAGGGCCACGGATTTCTTTAGAATCACTCTG
AGTTATACAAGGAATCAACCATTTAAAAAATACAA
TAAAAAAGCAATTACAAATATTTCTGTACCAGATT
AACACTGAAGGTGACTATCAGCCAACAAAAGGTTG
ACAGTTTTTCTAAGCTGTGGTTTTAGTTTACCTAT
TCCATTCTCCCTTTTCAGTTCTTATTTCCTATTCC
AAGACAACTGTATATCAGCTGTGAACTGCTGCATG
TGAAACATTCAAAACATGCCTCTACATAAAGTGGT
GGCTGCTGCAGAAGAATCTGAGTGGATAGCATATA
TAGCAGTTCTTACAGTGGGAGTATTTTTTTCTCAA
TTTGTTCATCCTTTTTCTTCTAACTATATTCTGCT
TATTGCTGTTCCAGTATTGTGTGATCACATCAAGG
GAGGGGTACCCTGTTATGCTTTATAAGTGTTAAGT
TTTGTGCTCCTGGGACCTAGCTCTGAAGCCTGGCT
AGGAGTGCAGTTCTCTGGGAAGCTTTCCTGTCTTT
CCTGAGCTAAGGTGGAACTCAGCAGTCATATTTTC
ATCTTTTGAAGTCATTGTCCCTTAAAGAATCTAAT
GCAAGCTATATAAAATTTTTACAAACCATTCTGGG
GTGGGGGGTTTTCACTGGCACTCTGAGACTTAGCC
CTCGACTGAATAGGGCAAGGGGCCCCCAACCTGGC
CATCCTCAGAAATAGGTGAAGAGCTTTTAAAAATG
TAACATTGCTAGAACCTATCCCAGGCTGACAGCCA
GGTGTTTTCTAGTGATGGGATTTAGGAATCTATAT
TGTAGCAGGATTTAACAGTATCTGATAACAGTATA
TTCTCTCTTCTTTCCTCTTCCTTTTTAAAGTTGAG
TTTGTTATTTGTACACATTCCTTACCCCTTATGGT
TTTATTGAACTCAAAAAAATTGAGCTGGAGTTTTG
TCATTTTATTGAGATTATAAATTCACTTAGGGGTA
ACTGACATCTTTAGAATACTAAATTGTTCCAACCA
AGACTTTCCCATTTTTATGGGTCATTTTCTTTTTT
TTTCTTTTTTTTTTTTTAATTTTTTTTTTTTTTTT
TTTTTTTTTTGGCCTTTTTTTGTCTTTTGTTGTTG
TTGCTATTTCTTGGACCGCTCCCGCGGCATATGGA
GGTTCCCAGGCTAGGGGTCGAATCGGAGCTGTAGC
CACCGGCCTACGCCAGAGCCACAGCAACGGTGGAT
CCGAGCCGCGTCTGCAACCTACACCACAGCTCACG
GCAACGCCGGATCGTTAACCCACTGAGCAAGGGCA
GGGACTGAACCCGCAACCTCATGGTTCCTAGTCGG
ATTCGTTAACCACTGCGCCACGACGGGAACTCCTT
TATGGGTCATTTTCTATCTTCTTTATTAATGTTTA

-continued

AATTTTTTCCCCAGTCTTAATTTCTCTTAAGTCAG
TCCTAGTTACATTACAGTTCTGGTTGAAATTATGG
CTATTTTATTAATTTTTTTCCTAGTTGATTATTGC
TGCTGTAGAGAAATGCTATTGATTTTTATAGGCCA
ATCTTGTATCCCACAACCTTGCCAAACTCTAGTAC
TGAGTCTAGTACTGAAGTCCCCTTGTGGCGCAGGG
GGTTAAGGATCAGGCATTGCAAGCAGCTGTGGTGC
AGGCTGCAATTGCAGAGTGGTTTCAATCCCTGGCC
CAGAAACTTCCACATGCCACAAGTACAGCCAAAAC
AAACAAACAAACAAACAAAAACTTGTGTCAGGTCT
GTTGAATTTTTTATGTATATGATCATCCAAATTCC
AAATAGTGACAGCTGGAGCTCTTTCCTTGCAGTTC
TTGCACCAGTTACTTCGTTGCTTACAGCGTTGGAA
GGACCTCCAGTCCCATGACAGTTGGCATCCTTGTC
TTGCTTCTGATTTTAAAGGGACTGCATTCCAAAGT
TATCTATTAAGTACTGTTTTGTGGTATAATCTTTA
TCAAGTTAAGGAAATTCCCTCCTATTCCTGGTCTA
CTAAAAGTATTTTTTTTAGTGATAAATAGATATTG
ACCTTTATCAAATACTTAATGTTTTAAAATGTATC
AGAGGATTAGGCCACAGAATGACTGTTCAGGAGTA
TCTTATATGAAATGTTATAACACAGCCAGGCATTC
AGAAACCCAGTCTCCATTCCCAGCAATCTCACTAA
TTAGCATTTTAATCGCAGATATGTCACTTGACTTA
GCTGAATCTTGGTGGCCTAATTTGTAGAGTGCGAG
ATTGGGATTAAATAATACAAGGTCTTTCTTATTTT
ATCACAAACAGAGATTTTCCATGGTCTCATTAAGT
TTTGAGTCTTCCTGGAGTTGCGGCTGTGGCTCAGT
GGTAGTGAACCTGACGGGTATCCATGAGGACATGG
TTCAATCCCTGGCCTTCTCAGTGGGTTAAGAATCC
AGCCTTGCTGTGAGCTGTGATGTAGGTCACAGAAG
TGGCTTGGATCCTGCGTTGCTGTGGCTGTGGTATA
GGCCAGCAGCTGTAGTTCCTATTTGACTCCTAGCC
AGGGAATTACTATATGCTGCAGGTGGGGCCCAAGT
TTTGAGTCTTCCGTATCCTTAGAAATGAGTCTCTC
CTTCAAAATGTAGTTGTTATTTTTTTATGCTTTTC
ATAAGTAGATGTTGCTTTTGTCATTCTCAACTGGT
TTTAAAACGATCCTGTCTTAATATAGTCTATGATT
ATCCAGCTTTACCTAGTATTCAGTGTTTAAGTACT
AATGGCAACATATGCCTGCTCCCCTTACACACTGT
TGCCTGTATCTCCAGACCCTGTTCATTCCTCAGCT
CCAGATTCCCCAAGCTAACTGCCTACTTGTCTCTC

-continued

TTGTCCCACATGCAGCTGGAGGATCGCATTGCCAA
AGCCACACCCCTCATTTGTCTCCCTCCAAATTTGC
TCCACCTTCTGTGTTCTGTCTACTCAATTGCCCGA
TCTGGAAACTTGGGTACCACCTCGATTCTTCCATA
CTCTTACTTTCCACATCAAACTGCAAGCCTTCCAG
AAGGTGCTAATCCACCTTGTTCAGGCCCCTGAGGT
GTTGGAACAGAATTGTGAGCAGTATGGAGGCGAAG
AGTTGAGCCCCATCAGCAAATGGATCCTGGTTAGG
TTCATTAACCGCTAAGCCATGAAGGGAACTCCCTA
ATTGGCATATTTTGAGCAGTTTGTGCTGATAATGT
TCAAATAAATTTTTATTTACACCAAGACCTTTCAA
AAGGTGTTTCTTGGTGACCTAGCAGGTTAAGGATC
CAGGGTTGTAACTGCTATGGCTCGGGTCAGTGCTG
TAGCATGGGTGAGCTTGATCCCTGGCTCTGGGACT
TCAGCATGCCATGCGTGCAGCCAAAAAAAAAAAAA
AATTTTTTTAATAAATGATAGTAGAAACAAATGAA
ATATTAACTACTTTATTTCTTTAATCATTCTTCCT
CTGAATATTATACAATTTAATCTTTAACTCTGAAG
GTTATGAAAAATAATTTTATATTTGATGCCACTTT
TATTTGAAGATACCCTGGTGCTGGGGATAAAACTA
GTATCAGGGTTATAGCATGTGCCGTTTTTGGTTTT
ATGGCACATGGTGTTTTGGAGTAGTACATGGTTTG
ACATGAGGTCCAGTAGAGTCTGTTTAATGGTCATT
CTATTCTGTGTCTTTAATCACTGCCCTTGGAACCC
AGCACCCAGGGTAAATGACATCTTCAGTCTGAAAG
GATGTTTAATTTGATGAATGTACATTGTTTATTCT
TAAGTTATTCTAGCCCTTTTATGTCTTAATATGTG
TCTTTTGCACCAAAAATTAGGAGGAAGTAACTCAC
TCATGAACTACCGAATGCCAAACTAAAACTTATTC
AGTGACTGAGTGACTGTAAATCTTGTGAACACAGA
CTTTCTTTTTTTTTTTATTAAAAATGTTCTTTTTA
AAAAAATTTTTTTTGGCCAACCACTCATGGCATGT
TTGATCAGGCCAGGGATCAAACCTGAGGCAGAGGC
GTAACCAGAGCCACAGCAGTGACAATGCTGAATCC
TTAACCTGCTGAGCCACCGGGGAACTCCTGAATGC
AGCCTTTCTTACCCCATTTTGAGCAGCCTCATTTG
TCTGCCTATAGAAAGAAAGATGAATTTATAGATGG
GCTTGCAAAATCTTGCATGTTTTCTGTTTCCAAAA
ACTGTTGAGAATTCCTTTGAGGAAATTATTGTAGG
TATTTATATATTCAGAGGATATTAATTTCTTTACT

-continued

TAATAGATACTTATTGTGTACCTGCCCTATACCAG
GCACTGCCCAAGCCCCTGAGGATATAGCAGCAAAC
AAAAGAGACTCATTCCCTGCTTACATTCCCACTCA
AGGAAGAAGGACACAAGTCAGCTATTTAAAAATTA
TTTCATGATCTCAACACCTACCTGGGGGCTTCACT
TCCAGAGGGGCCTGCCAGGTCCCTCAAGGTAGTCC
ACACAGCAGTTAGGGCCTTGGCTTCACTCCCAGCC
CCAGCCCCCACAAGTGACCGCTCAGGTACAAAGGA
ATGAGTCTGTGCGTAGAGGGTTCCCCTTGGCACAG
GGGCCCTAGGCCCCATAGGTGCTGATAGCCCTCAT
TATAGCCCCATTAGCAGAGCTGCCAGGGTCCCTAC
AAGAAGGTGCCTGGTTACAAGAATTATTACTTTAC
TTATTTATGCACCATGTGGAAGTTTCCAGGCTAGA
AGTCGAATCAGAGATGTAGCTGCTGGCCTACGCCA
CAGCCATACCAGATCTGAGCTGCATCTGCGACCTC
ACCACAGCACACGGCAAGGCCAGGGATCGAACCCG
CGTCCTCATGGATACTAATCCATGGCTGGTTTCTG
CTGAGTCATGATGGGAACTCCCAGAATCACAAAAG
CTCAAAGCTGTGGCAAACCCACCAGGTGTTTATTG
GTTTTTCCAGTTTAGATACAATGTATCAAGCAGAG
GTTATTTTTACCATAAGCATGTTGCTGGCATTCCA
CCTTTATCTTTTCTAAGAAACAGAGCCAGAAAATT
ATCTGAAGGTCAAATTTGTCCTTAGAGAAGGAGAA
AGAGTTGAGTTAACCCTTCACCTACAGTTGTTTTT
GTTGTAAGTGTTGCACAGGAGACAAATGGAGTATA
AAGAACATTCACAGCTGATGCCGCTACTATGTTCA
TTATGCTGCAGACATTAAGTGATTTCAATATAAAC
AGGACACTGACACCCTCTTTATTTTGTATTTTGCA
GATAAGTAATCATGGTGAAAAGCCATATAGGTGGC
TGGATCCTCGTTCTCTTTGTGGCCGCATGGAGTGA
CATAGGGCTCTGCAAGAAGCGACCAAAGCCTGGCG
GAGGATGGAACACTGGGGGGAGCCGATACCCAGGG
CAGGGTAGTCCTGGAGGCAACCGCTATCCACCCCA
GGGAGGGGGTGGCTGGGGACAGCCCCACGGAGGTG
GCTGGGGACAGCCCCACGGAGGCGGCTGGGGACAG
CCCCACGGTGGCGGCTGGGGACAGCCCCATGGTGG
CGGAGGCTGGGGTCAAGGTGGTGGCTCCCACGGTC
AGTGGAACAAGCCCAGTAAGCCGAAAACCAACATG
AAGCATGTGGCAGGCGCCGCTGCAGCTGGGGCAGT
GGTAGGGGGCCTCGGCGGTTACATGCTGGGGAGTG
CCATGAGCAGACCCCTGATACACTTTGGCAGTGAC

-continued

TATGAGGACCGTTACTATCGTGAAAACATGTACCG
TTACCCCAACCAAGTGTACTACAGGCCAGTGGATC
AGTACAGCAACCAGAACAGTTTTGTGCATGACTGC
GTCAACATCACCGTCAAGCAGCACACAGTGACCAC
GACCACCAAGGGGGAGAACTTCACCGAGACGGACG
TCAAGATGATAGAGCGCGTGGTGGAACAGATGTGC
ATCACCCAGTACCAGAAAGAGTACGAGGCGTACGC
CCAAAGAGGGGCCAGTGTGATCCTCTTCTCCTCCC
CTCCTGTGATCCTCCTCATCTCTTTCCTCCTTTTC
CTCATAGTGGGCTGAGGGTGGCCTTTCTGTCGGCA
TCATCTTCTTAATCTTTATCAGGTTGGGGGAGGGA
ATATCTACCTGCAGCCCTTTAGTGGTGGTGTCTCA
TTCTTGCTTCTCTCTTCGGCACCCATAGGCTAACA
TCCATGGCGCTTGTAGCACTGGAAAAGGAGAGTAG
ACCTGAGATGTGATGTATTTAAGCCCCATTTGATT
GAATCCTTCATAGGCCAGTGCTAGTGCTGGACTGG
TAAGAGCGTAACAGCAAATAATCATTGGTTGATCT
GGGCTCATTTTTTGTCTGGTGCAACAGATTGAGGC
TAAAACAATTCTCAAAACACACTTCAAGTACCTTT
ACCTAAATACCTCCAGCTCCTTCTCCAGCTAGAGC
TCAGTACACAAATGCCCCGCCATAGTAGTGATTTT
GTAGCAACTTTCCCATTTAAGAAAACCTGACTACA
TTTTCCTGTTCAAATAGCATTTCTACTGAGTTGGG
GAGGAGGCCACATAATACTCATTCAAAAAAATGAA
ACTGGAAATCCTTAGCTCCTGGGCCCAGGGTCAGC
CCAGTGGAAAGCATGTGTCCTGTGTCTGCAGAGAA
CTAAGGATATTTTGCAATTTGCAGTACAGGTTACA
CAGCAGCTATTGCATCAAGAATGGATGTCTGTGCA
ACACTAGACTTCTGGGCAGAGGGCATTTTCACAGG
CAATGAACATAACTCACATAATATGAAAGGCTCTG
AAACTTAAAAAATTCCCACCTGTGTGAGGAACCCT
CAGAGGCAGCCTTCTGTTATGGATGTTTAAAGCAC
CTTCATGGGGTAGTTCTTTCTTTAGTAATACAAAC
TATAGATAATTAAGGTAGTAGGACATGAAACAATC
TTCTGGACATTGAGAACAAATCTCTTTTGTTTGTT
TATCTGGGAACTGGAGTGATTTTGCCATTTCTTGG
ATGAAGCCAGGAGATTTTAACATAGAGGAAGCTGC
AGCTATAAAAACATCATATTTATTCATTTGATTGA
GTCTTTCATGGGCCAGTGCCGGTGTTGGGCTAGCA
AGCATATGATACCAAATATAGAGGGTTATGAAGAA

-continued

AATGATTAGTGTACAAAAAAGAGAAATGCTTACAT
TTCTTTATTGCTGTGTCATAATTGTCAAAAATCAG
AATTAGGTCCTCAATTTCTATAATTGGCTTTTGAA
TCAAAGAATAGGAAGGCATTCCCCCCCAAAAAAGT
TAAAGATGATAGAAATATGATCCATTCATATTAGG
AAAAGAAATTCTGGTACTGTTATTTAAATAAGGCA
AAATTATTCCCTGGATTGTTTGGTGTTGTCACCTA
GCAGATATACATTACTCTTCTGCATTGTTATTGGC
TTGCACTTTGTGGGTATCCTATGTAAAAAAAATAT
ATGTATATATATATATTGCATATGACAAACTTGGA
GATTTTGGTTAGAGCTGTTAACATCTGAATTATCA
AATGCATTACTTGTTTTTGTAAGGTACTAAATATT
TAATAATACTTAAAGGAAACCCTTTTGTGTGGTCC
TTCGGCTTACAATGTGCACTGAATAGTTTTGTATA
AGGATCCAGAGTGGCATTTGAAATTCGCATGTGCT
TTATATTTTCTATATTTGTAACTTTGCATGTACTT
GTTTTATTGTATTAAAAGTTTATAAATGTTTATTA
TCTGACTAAATTAAAACAGGAGCTACAATGAG

SEQ ID NO: 2 500 bp of upper homologous arm

CTTGGCACAGGGGCCCTAGGCCCCATAGGTGCTGATAGCCCTCATTATAG
CCCCATTAGCAGAGCTGCCAGGGTCCCTACAAGAAGGTGCCTGGTTACAA
GAATTATTACTTTACTTATTTATGCACCATGTGGAAGTTTCCAGGCTAGA
AGTCGAATCAGAGATGTAGCTGCTGGCCTACGCCACAGCCATACCAGATC
TGAGCTGCATCTGCGACCTCACCACAGCACACGGCAAGGCCAGGGATCGA
ACCCGCGTCCTCATGGATACTAATCCATGGCTGGTTTCTGCTGAGTCATG
ATGGGAACTCCCAGAATCACAAAAGCTCAAAGCTGTGGCAAACCCACCAG
GTGTTTATTGGTTTTTCCAGTTTAGATACAATGTATCAAGCAGAGGTTAT
TTTTACCATAAGCATGTTGCTGGCATTCCACCTTTATCTTTTCTAAGAAA
CAGAGCCAGAAAATTATCTGAAGGTCAAATTTGTCCTTAGAGAAGGAGAA
AGAGTTGAGTTAAC

SEQ ID NO: 3 1000 bp lower homologous arm

CGGTTACATGCTGGGGAGTGCCATGAGCAGACCCCTGATACACTTTGGCA
GTGACTATGAGGACCGTTACTATCGTGAAAACATGTACCGTTACCCCAAC
CAAGTGTACTACAGGCCAGTGGATCAGTACAGCAACCAGAACAGTTTTGT
GCATGACTGCGTCAACATCACCGTCAAGCAGCACACAGTGACCACGACCA
CCAAGGGGGAGAACTTCACCGAGACGGACGTCAAGATGATAGAGCGCGTG
GTGGAACAGATGTGCATCACCCAGTACCAGAAAGAGTACGAGGCGTACGC
CCAAAGAGGGGCCAGTGTGATCCTCTTCTCCTCCCCTCCTGTGATCCTCC
TCATCTCTTTCCTCCTTTTCCTCATAGTGGGCTGAGGGTGGCCTTTCTGT

-continued

CGGCATCATCTTCTTAATCTTTATCAGGTTGGGGAGGGAATATCTACCT

GCAGCCCTTTAGTGGTGGTGTCTCATTCTTGCTTCTCTCTTCGGCACCCA

TAGGCTAACATCCATGGCGCTTGTAGCACTGGAAAAGGAGAGTAGACCTG

AGATGTGATGTATTTAAGCCCCATTTGATTGAATCCTTCATAGGCCAGTG

CTAGTGCTGGACTGGTAAGAGCGTAACAGCAAATAATCATTGGTTGATCT

GGGCTCATTTTTTGTCTGGTGCAACAGATTGAGGCTAAAACAATTCTCAA

AACACACTTCAAGTACCTTTACCTAAATACCTCCAGCTCCTTCTCCAGCT

AGAGCTCAGTACACAAATGCCCCGCCATAGTAGTGATTTTGTAGCAACTT

TCCCATTTAAGAAAACCTGACTACATTTTCCTGTTCAAATAGCATTTCTA

CTGAGTTGGGGAGGAGGCCACATAATACTCATTCAAAAAAATGAAACTGG

AAATCCTTAGCTCCTGGGCCCAGGGTCAGCCCAGTGGAAAGCATGTGTCC

TGTGTCTGCAGAGAACTAAGGATATTTTGCAATTTGCAGTACAGGTTACA

CAGCAGCTATTGCATCAAG

SEQ ID NO: 4 Green fluorescent protein encoding sequence

ATGGTGAGCAAGGGCGAGGAGCTGTTCACCGGGGTGGTGCCCATCCTGGT

CGAGCTGGACGGCGACGTGAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

-continued

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCACGGCA

TGGACGAGCTGTACAAGTAA

SEQ ID NO: 5, 6, 7, 8 primers used to obtain the upper and lower arms

PRNP upper arm MluI for: CTAGACGCGTCTTGGCACA-GGGGCCCTAG

PRNP upper arm BsiW1 rev:

GACTA*CGTACG*<u>CCTACCACTGCCCCAGCTG</u>

PRNP lower arm XhoI for: GACTCTCGAGCGGTTACAT-GCTGGGGAGT

PRNP lower arm AscI rev: GTCAGGCGCGCCTTGATG-CAATAGCTGCTGT

Targeting vector is generated by digesting with AscI (introduced by the primer) and HpaI enzyme on the endogenous sequence.

SEQ ID NO: 9 and 10 primers inside and outside vector to confirm GFP Inside the GFP expression vector: CCA-GCTGGGGCTCGACTAGA Outside the homology arm: CCATTTTGAGCAGCCT-CATTTG SEQ ID NO: 11 LoxP nucleotide sequence

ATAACTTCGTATAATGTATGCTATACGAACGGTA

SEQ ID NO: 12: single stranded oligo used to target ZBED

GGTGGCAGAA GGAGTGGATA AAGAGGCAAA ATTGCCTGCC

AAAAAGAAAA GAAAGAAGGGTTTGC (EcoR1 site follows in italics) *GAATTC* (LoxP site follows in lower case) <u>taccgttcgtatagcatacattatacgaagttat</u> AGGGGAAAA

GGCGACGAAA GAAACTGATC CTTGCAAAAA AGTTTAGTAA

GGATTTGGGA TCTGGGAGGC CTGTTGCAAG

SEQ ID NO: 13 is the ZBED6 sequences shown in FIG. 6 with the EcoRI and LoxP insert Blastocyst 1 and 5

AGAAGGGTTTGC<u>GAATTC</u>TACCGTTCGTATAGCATACATTATACGAAGTTATAGGGGAAAAGGCGAC

SEQ ID NO: 14 and 15 flanking sequence for ss oligo

Upper:
GGTGGCAGAA GGAGTGGATA AAGAGGCAAA
ATTGCCTGCCAAAAAGAAAA GAAAGAAGGGTTTGCGAATTC Lower:

AGGGGAAAA GGCGACGAAA GAAACTGATC CTTGCAAAAA
AGTTTAGTAA GGATTTGGGA TCTGGGAGGC CTGTTGCAAG

SEQ ID NO:16

ZBED insert from Balstocyst 3 and 4 from FIG. 6

AGAAGGGTTTGC<u>GAATCC</u>TACCGTTCGTATGCATACATTATACGAAGTTA
AGGGGAAAAGGCGAC

SEQ ID NO:17

ZBED insert blastocyst 2 from FIG. 6

AGAAGGGTTTGC<u>GAATTC</u>TACCGTTCGTATGCATACATTATACGAAGT
TAAGGGGAAAAGGCGGC

What is claimed is:

1. A method of targeted gene editing of an animal genome, the method comprising:

a) producing a zygote comprising said genome of said animal by fertilizing animal oocyte and animal spermatozoa;

b) injecting into the cytoplasm of said zygote a composition one or more vectors comprising:

i) a nuclease;

ii) at least one guide nucleic acid molecule that targets said nuclease to a target nucleic acid of said genome at a target sequence;

iii) a single stranded oligonucleotide or double stranded nucleic acid molecule comprising a heterologous nucleic acid molecule of interest (NOI);

iv) a sequence homologous to a first flanking sequence upstream of said target sequence and a second sequence comprising a second flanking sequence downstream of said target sequence, wherein said first and second flanking sequences comprise about 50 nucleotides or less when said first and second flanking sequence comprise a single stranded oligonucleotide and said first and second flanking sequences comprise about 1000 nucleotides or less when said first and second flanking sequences comprise a double stranded oligonucleotide;

c) said composition injected into said cell before said zygotic cell forms a single nucleus;

d) said nuclease introducing a double stranded break at said target sequence of said target gene of said animal genome; and e) said NOI recombined into said target sequence of said target nucleic acid of said animal genome;

f) wherein said zygote has pronuclei that cannot be visually observed by the unaided human eye or by a microscope unaided by contrast; and wherein said animal is a swine or ruminant animal.

2. The method of claim 1, where the composition is injected into the cytoplasm of said zygotic cell.

3. The method of claim 1, wherein said composition is injected up to 24 hours after fertilization.

4. The method of claim 1, wherein said composition is injected at least three hours to 16 hours after fertilization.

5. The method of claim 1, wherein said composition is injected 12 to 16 hours after fertilization.

6. The method of claim 1, wherein said composition is injected 16 hours after fertilization.

7. The method of claim 1, where expression of said target gene is modified.

8. The method of claim 1, wherein said NOI expresses a polypeptide.

9. The method of claim 1, wherein at least one phenotype of said animal is modified after said NOI is recombined into said animal genome.

10. The method of claim 1, wherein said animal is a ruminant animal.

11. The method of claim 1, wherein said animal is swine or bovine.

12. The method of claim 1, wherein said animal is swine.

13. The method of claim 1, wherein said composition comprises a single stranded oligonucleotide comprising said NOI.

14. The method of claim 13, wherein said flanking sequences comprise 50 or fewer base pairs.

15. The method of claim 1, wherein said composition comprises a double stranded nucleic acid molecule comprising said NOI.

16. The method of claim 15, wherein said flanking sequences comprise 1000 or fewer base pairs.

17. The method of claim 1, wherein said composition comprises a Clustered Regularly Interspaced Short Palindromic Repeat (CRISPR)—CRISPR associated (Cas) system comprising one or more expression vectors comprising a guide RNA that hybridizes with said target gene and a Cas9 protein.

18. A method of targeted gene editing of an animal genome of an animal having pronuclei that cannot be visually observed by the unaided human eye or by a microscope unaided by contrast, the method comprising:

a) producing a zygote comprising said genome of said animal by fertilizing animal oocyte and animal spermatozoa;

b) injecting into said zygote a composition comprising one or more vectors comprising:

i) at least one nucleotide sequence encoding a Clustered Regularly Interspaced Short Palindromic Repeat (CRISPR)—CRISPR associated (Cas) system comprising one or more expression vectors comprising:

a guide RNA that hybridizes with a target sequence of said animal; and a nucleotide sequence encoding a Cas9 protein;

ii) a single stranded oligonucleotide or double stranded nucleic acid molecule comprising a heterologous nucleic acid molecule of interest (NOI);

iii) a sequence homologous to a first flanking sequence upstream of said target sequence and a second sequence comprising a second flanking sequence downstream of said target sequence wherein said first and second flanking sequences comprise about 50 nucleotides or less when said first and second flanking sequence comprise a single stranded oligonucleotide and said first and second flanking sequences comprise about 1000 nucleotides or less when said first and second flanking sequences comprise a double stranded oligonucleotide;

c) said composition injected into said cell before said zygotic cell forms a single nucleus;

d) said nuclease introducing a double stranded break at said target sequence of said target nucleic acid of said animal genome;

e) said NOI recombined into said target sequence of said target nucleic acid of said animal genome; and wherein at least 80% to 100% of said zygotes comprise a recombination event and/or non-homologous end joining; and wherein said animal is a swine or ruminant animal.

19. A method of targeted nucleic acid editing of an animal genome, the method comprising:

a) producing a zygote comprising said genome of said animal by fertilizing animal oocyte with animal spermatozoa;

b) injecting into said zygote a composition comprising:

i. a nuclease enzyme or a nucleic acid encoding a nuclease, wherein said nuclease can introduce a double strand break; and ii. one or more nucleic acids and/or expression vectors, comprising:

a first sequence homologous to a first flanking sequence upstream of a target sequence; and a second sequence comprising a second flanking sequence downstream of said target sequence, wherein said first and second flanking sequences comprise about 50 nucleotides or less when said first and second flanking sequence comprise a single stranded oligonucleotide and said first and second flanking sequences comprise about 1000 nucleotides or less when said first and second flanking sequences comprise a double stranded oligonucleotide;

wherein said composition is injected into said zygote about 12 to 16 hours after fertilization; and wherein said animal having pronuclei that cannot be visually observed by the unaided human eye or by a microscope unaided by contrast; and wherein said animal is a swine or ruminant animal.

20. The method of claim 19, where the composition is injected into the cytoplasm of said zygotic cell.

21. The method of claim 19, wherein the composition further comprises a single stranded or double stranded nucleic acid molecule comprising a heterologous nucleic acid molecule of interest (NOI).

22. The method of claim 19, wherein expression and/or function of said target sequence is modified.

23. The method of claim 19, wherein said animal is swine or bovine.

24. The method of claim 19, wherein said animal is swine.

25. The method of claim 19, wherein said composition comprises a Clustered Regularly Interspaced Short Palindromic Repeat (CRISPR)—CRISPR associated (Cas) nuclease and further comprising a guide RNA that hybridizes with said target sequence and a Cas9 protein.

26. The method of claim 25, wherein said Cas9 nuclease and said guide RNA are encoded in one or more nucleic acids and/or expression vectors.

27. The method of claim 1 wherein at least 80% to 100% of said zygotes comprise a recombination event and/or non-homologous end joining.

28. The method of claim 19 wherein at least 80% to 100% of said zygotes comprise a recombination event and/or non-homologous end joining.

* * * * *

SEQUENCE LISTING

<160> NUMBER OF SEQ ID NOS: 17

<210> SEQ ID NO 1
<211> LENGTH: 10988
<212> TYPE: DNA
<213> ORGANISM: Sus scrofa
<220> FEATURE:
<221> NAME/KEY: misc_feature
<222> LOCATION: (718)..(817)
<223> OTHER INFORMATION: n is a, c, g, or t
<220> FEATURE:
<221> NAME/KEY: misc_feature
<222> LOCATION: (2967)..(2968)
<223> OTHER INFORMATION: n is a, c, g, or t
<220> FEATURE:
<221> NAME/KEY: misc_feature
<222> LOCATION: (2993)..(2993)
<223> OTHER INFORMATION: n is a, c, g, or t

<400> SEQUENCE: 1
acgtacgcgg ccaaaagagt ctcaactccc tcccagagac tcagatttcc gaccagcttg 60
gcagatcccg ggcgccggag cgccagagcg cgcgcgcgcg ccgccgccgc ctcccttccc 120
cgcccgcgcg cctcgccacc cctcggcgcc agacactgac agccccggag ctgcgagcgt 180
cttctgttcc agcggtggca ggtaaacagc cgggtcgccc cgagaactgg gggtgccaag 240
gtcgggagtc agaacccccc gccttggagc ttaggcgcaa gggtgagcgg cccacttggg 300
gcgctaggga aaccttgaca gagagggggg cgggggactt ccggcgggcg gggggcgcga 360
caggcctgcc cccgcttgtt cgtcggctta acattggccc cgctcacatt tgctttccag 420
gtggggtgag ggccctttac tcggaatggg gcttggtggg ggaagggggt gcctggggct 480
ggccgcgacc cctgggcagg gaggcggatg gtggcgggga gtctagccct ctcccacgcg 540
cgtccgcggc tggcggagga tgggagaggc gcgccggcac cggggccgca gggccgggaa 600
ctcaaggagg gtcgcccacg gcctccgctg aggcgctcgg aggagaacca gggagagggg 660
ccggcgtgcg gctctcccga ggccccaggg gcacgtgggg tggggatgat ggccccgnnn 720
nnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnagc cccaaggggc ccgttggggg 840
ggggtgatgg cccaggcccc ggcgggaggg gcccttgccg ccgccaccat ggagctcctc 900
cggagagacg gcccacctgc catccacgcg gcccgggggt gctggggagg ccgcagcggg 960
gtgggcctcc tgcatccctg gggatggaga ccgggcacgt ggtccgacct tcgggcctcg 1020
gcgggcggag tctcgggcgg ccccaccctc actgtcggcc gagacgtcca ggtccctggg 1080
ggccgagtgt ccggagagcc caggtgcttt gcttttcact gtctccactg cccctccccg 1140
aagggaactg ggcggtcaga ggctcctctc aaggggatca gggccggaca gctctcctcc 1200
tgatccactt gtgtgggctg ccctttcagg cttgattgta aacaacgagg agaagtccat 1260
ttttactgtc ccttttcatt tttttccctt ttctaaattt gtagcaacca tggcaaatca 1320
gtttttaaaa tcataaccca cagccatcaa tccaccctta ccatctcaaa gccactgctt 1380
tctgtttttc agttttctgt ctccagattc gtacataacg caaagaaatt tcaactgccc 1440
tgattatgat tatcctcctc taatggccga gttattttct tctgcttaaa gcgtcgcagt 1500
ttaataagca gttccccgaa tgctgaacat ttgaaatgtt tcgttttttc ttgcaaaaaa 1560
accttccagg tataacagta ttaaagaaag aataggaata ggagttccct ggtggcctgg 1620
tggttaagga tcccatattg tcgctgctgt ggctagagtt ccatccctgg cccggaaact 1680
tctgtatacc tcaggcaagc caacaaaaag aaaaaaagaa gggaagaaaa gaaaaaaata 1740

-continued

```
gtaacagaaa attgaattaa aatgtcaaac ccctggaaaa attaacaact atctcagatt   1800
tgaggaagaa aaaaaaaatc aacagtttta cctgcagtaa acactgaggc gctcttacaa   1860
tgaaaaagaa ctaaccggaa agggaaagaa agcagagcta ggatgtgatt tgtatatgat   1920
ttgtatctga cacaaaattt tcatagttat gaaaggaaaa tatgaaaatt ataataaatg   1980
atgaatcaat tatagaataa aatgtaaatt aaagcactct ggattatcat tttacaatta   2040
ctaacaaata caacaacagt aatagtaaca gcaaccactg ttggaagatt gcctagaaat   2100
tttcacattc agttattttg agaggtggca ggactttggg gttagaagaa tggctctgca   2160
cctaatttca tagcatggaa tgggttacct aatttcctca tcctcctttt gtgcattcat   2220
aaaatagagg aaattatacc tacttcagga aattgctaag attaaccatc tatgtaaaac   2280
tgacctttgg tatgtaatcc tttttctatt cttgggcaca ctgcactggg gacattgtga   2340
atttactgta aagcaatttg gtaatgcatt aggccatgac ccagaattta cctgcaatgg   2400
aagaaacaac aagaaaaaaa aggggggaa aaaaaagcca tatgcagtca cagaattcag   2460
aatgatctaa aattagaccc aacggaaaaa caacctaaat gtataacagc agggcagcag   2520
ctgaggaaat catggctctt taactgaaag aaacattatg taactatcaa aagtcggtgg   2580
tacatgagaa aaaactgata aatcagtgta gattacatta ccaaactgta tctacttact   2640
cagtgaatgc atatgtggaa aatctgaaag gaaaagcata caaaggaatt gaatagaatt   2700
aaaatgaagt tagaaattat gggtcagttt aattttcttt tttatttata tactgctttt   2760
ctaagtaacg aaatttttaa gataattatt catcgttctc aatttttgta atgaaatgga   2820
gccatagttt tctgtatgtg ggagagggag agctcagtgt catgttagct gacttcattt   2880
cttcagatat tgtctctttt tttttctcgt gtagatggat tagggggtta gtaatgtata   2940
tattaggatc cttctttaag gaatagnntc taaaaattat tatcaattct agnttttct    3000
tttttggtg tttctaagga ccctgaatat atttgaaaac tgaacagttt cagctaagcc    3060
gaagcattct gtcttcccca gaacacaaat ccagcctcgc tgagccatta cagatgtaca   3120
tactgcagag tccctttgat ctcgtgatgg ctcagagtcc ctatctgtca cagaaaagaa   3180
gggcctagaa aggctatgat gacagtcctt gctctgaggc aacttagggt tatatgtgta   3240
acccacacct cttaaatcat cctttcttgt aaaatcattt tgattttgca ggcaaagggc   3300
cacggatttc tttagaatca ctctgagtta tacaaggaat caaccattta aaaaatacaa   3360
taaaaaagca attacaaata tttctgtacc agattaacac tgaaggtgac tatcagccaa   3420
caaaaggttg acagttttc taagctgtgg ttttagttta cctattccat tctccctttt    3480
cagttcttat ttcctattcc aagacaactg tatatcagct gtgaactgct gcatgtgaaa   3540
cattcaaaac atgcctctac ataaagtggt ggctgctgca gaagaatctg agtggatagc   3600
atatatagca gttcttacag tgggagtatt tttttctcaa tttgttcatc ctttttcttc   3660
taactatatt ctgcttattg ctgttccagt attgtgtgat cacatcaagg gaggggtacc   3720
ctgttatgct ttataagtgt taagttttgt gctcctggga cctagctctg aagcctggct   3780
aggagtgcag ttctctggga agctttcctg tctttcctga gctaaggtgg aactcagcag   3840
tcatattttc atcttttgaa gtcattgtcc cttaaagaat ctaatgcaag ctatataaaa   3900
tttttacaaa ccattctggg gtgggggtt ttcactggca ctctgagact tagccctcga    3960
ctgaataggg caaggggccc ccaacctggc catcctcaga aataggtgaa gagcttttaa   4020
aaatgtaaca ttgctagaac ctatcccagg ctgacagcca ggtgttttct agtgatggga   4080
```

-continued

```
tttaggaatc tatattgtag caggatttaa cagtatctga taacagtata ttctctcttc   4140
tttcctcttc ctttttaaag ttgagtttgt tatttgtaca cattccttac cccttatggt   4200
tttattgaac tcaaaaaaat tgagctggag ttttgtcatt ttattgagat tataaattca   4260
cttaggggta actgacatct ttagaatact aaattgttcc aaccaagact ttcccatttt   4320
tatgggtcat tttctttttt tttctttttt ttttttaat ttttttttt tttttttttt   4380
tttttggcct ttttttgtct tttgttgttg ttgctatttc ttggaccgct cccgcggcat   4440
atggaggttc ccaggctagg ggtcgaatcg gagctgtagc caccggccta cgccagagcc   4500
acagcaacgg tggatccgag ccgcgtctgc aacctacacc acagctcacg gcaacgccgg   4560
atcgttaacc cactgagcaa gggcagggac tgaacccgca acctcatggt tcctagtcgg   4620
attcgttaac cactgcgcca cgacgggaac tcctttatgg gtcattttct atcttcttta   4680
ttaatgttta aattttttcc ccagtcttaa tttctcttaa gtcagtccta gttacattac   4740
agttctggtt gaaattatgg ctattttatt aatttttttc ctagttgatt attgctgctg   4800
tagagaaatg ctattgattt ttataggcca atcttgtatc ccacaacctt gccaaactct   4860
agtactgagt ctagtactga agtccccttg tggcgcaggg ggttaaggat caggcattgc   4920
aagcagctgt ggtgcaggct gcaattgcag agtggtttca atccctggcc cagaaacttc   4980
cacatgccac aagtacagcc aaaacaaaca aacaaacaaa caaaaacttg tgtcaggtct   5040
gttgaatttt ttatgtatat gatcatccaa attccaaata gtgacagctg gagctctttc   5100
cttgcagttc ttgcaccagt tacttcgttg cttacagcgt tggaaggacc tccagtccca   5160
tgacagttgg catccttgtc ttgcttctga ttttaaaggg actgcattcc aaagttatct   5220
attaagtact gttttgtggt ataatcttta tcaagttaag gaaattccct cctattcctg   5280
gtctactaaa agtatttttt ttagtgataa atagatattg acctttatca aatacttaat   5340
gttttaaaat gtatcagagg attaggccac agaatgactg ttcaggagta tcttatatga   5400
aatgttataa cacagccagg cattcagaaa cccagtctcc attcccagca atctcactaa   5460
ttagcatttt aatcgcagat atgtcacttg acttagctga atcttggtgg cctaatttgt   5520
agagtgcgag attgggatta aataatacaa ggtctttctt attttatcac aaacagagat   5580
tttccatggt ctcattaagt tttgagtctt cctggagttg cggctgtggc tcagtggtag   5640
tgaacctgac gggtatccat gaggacatgg ttcaatccct ggccttctca gtgggttaag   5700
aatccagcct tgctgtgagc tgtgatgtag gtcacagaag tggcttggat cctgcgttgc   5760
tgtggctgtg gtataggcca gcagctgtag ttcctatttg actcctagcc agggaattac   5820
tatatgctgc aggtggggcc caagttttga gtcttccgta tccttagaaa tgagtctctc   5880
cttcaaaatg tagttgttat ttttttatgc ttttcataag tagatgttgc ttttgtcatt   5940
ctcaactggt tttaaaacga tcctgtctta atatagtcta tgattatcca gctttaccta   6000
gtattcagtg tttaagtact aatggcaaca tatgcctgct cccettacac actgttgcct   6060
gtatctccag accctgttca ttcctcagct ccagattccc caagctaact gcctacttgt   6120
ctctcttgtc ccacatgcag ctggaggatc gcattgccaa agccacaccc ctcatttgtc   6180
tccctccaaa tttgctccac cttctgtgtt ctgtctactc aattgcccga tctggaaact   6240
tgggtaccac ctcgattctt ccatactctt actttccaca tcaaactgca agccttccag   6300
aaggtgctaa tccaccttgt tcaggcccct gaggtgttgg aacagaattg tgagcagtat   6360
ggaggcgaag agttgagccc catcagcaaa tggatcctgg ttaggttcat taaccgctaa   6420
gccatgaagg gaactcccta attggcatat tttgagcagt ttgtgctgat aatgttcaaa   6480
```

-continued

```
taaattttta tttacaccaa gacctttcaa aaggtgtttc ttggtgacct agcaggttaa   6540
ggatccaggg ttgtaactgc tatggctcgg gtcagtgctg tagcatgggt gagcttgatc   6600
cctggctctg ggacttcagc atgccatgcg tgcagccaaa aaaaaaaaaa aattttttta   6660
ataaatgata gtagaaacaa atgaaatatt aactacttta tttctttaat cattcttcct   6720
ctgaatatta tacaatttaa tctttaactc tgaaggttat gaaaaataat tttatatttg   6780
atgccacttt tatttgaaga taccctggtg ctggggataa aactagtatc agggttatag   6840
catgtgccgt ttttggtttt atggcacatg gtgttttgga gtagtacatg gtttgacatg   6900
aggtccagta gagtctgttt aatggtcatt ctattctgtg tctttaatca ctgcccttgg   6960
aacccagcac ccagggtaaa tgacatcttc agtctgaaag gatgtttaat ttgatgaatg   7020
tacattgttt attcttaagt tattctagcc cttttatgtc ttaatatgtg tcttttgcac   7080
caaaaattag gaggaagtaa ctcactcatg aactaccgaa tgccaaacta aaacttattc   7140
agtgactgag tgactgtaaa tcttgtgaac acagactttc tttttttttt tattaaaaat   7200
gttcttttta aaaaaatttt ttttggccaa ccactcatgg catgtttgat caggccaggg   7260
atcaaacctg aggcagaggc gtaaccagag ccacagcagt gacaatgctg aatccttaac   7320
ctgctgagcc accggggaac tcctgaatgc agcctttctt accccatttt gagcagcctc   7380
atttgtctgc ctatagaaag aaagatgaat ttatagatgg gcttgcaaaa tcttgcatgt   7440
tttctgtttc caaaaactgt tgagaattcc tttgaggaaa ttattgtagg tatttatata   7500
ttcagaggat attaatttct ttacttaata gatacttatt gtgtacctgc cctataccag   7560
gcactgccca agcccctgag gatatagcag caaacaaaag agactcattc cctgcttaca   7620
ttcccactca aggaagaagg acacaagtca gctatttaaa aattatttca tgatctcaac   7680
acctacctgg gggcttcact tccagagggg cctgccaggt ccctcaaggt agtccacaca   7740
gcagttaggg ccttggcttc actcccagcc ccagccccca caagtgaccg ctcaggtaca   7800
aaggaatgag tctgtgcgta gagggttccc cttggcacag gggccctagg ccccataggt   7860
gctgatagcc ctcattatag ccccattagc agagctgcca gggtccctac aagaaggtgc   7920
ctggttacaa gaattattac tttacttatt tatgcaccat gtggaagttt ccaggctaga   7980
agtcgaatca gagatgtagc tgctggccta cgccacagcc ataccagatc tgagctgcat   8040
ctgcgacctc accacagcac acggcaaggc cagggatcga acccgcgtcc tcatggatac   8100
taatccatgg ctggtttctg ctgagtcatg atgggaactc ccagaatcac aaaagctcaa   8160
agctgtggca aacccaccag gtgtttattg gtttttccag tttagataca atgtatcaag   8220
cagaggttat ttttaccata agcatgttgc tggcattcca cctttatctt ttctaagaaa   8280
cagagccaga aaattatctg aaggtcaaat ttgtccttag agaaggagaa agagttgagt   8340
taacccttca cctacagttg tttttgttgt aagtgttgca caggagacaa atggagtata   8400
aagaacattc acagctgatg ccgctactat gttcattatg ctgcagacat taagtgattt   8460
caatataaac aggacactga caccctcttt attttgtatt ttgcagataa gtaatcatgg   8520
tgaaaagcca tataggtggc tggatcctcg ttctctttgt ggccgcatgg agtgacatag   8580
ggctctgcaa gaagcgacca aagcctggcg gaggatggaa cactgggggg agccgatacc   8640
cagggcaggg tagtcctgga ggcaaccgct atccacccca gggagggggt ggctggggac   8700
agccccacgg aggtggctgg ggacagcccc acggaggcgg ctggggacag ccccacggtg   8760
gcggctgggg acagccccat ggtggcggag gctggggtca aggtggtggc tcccacggtc   8820
```

-continued

```
agtggaacaa gcccagtaag ccgaaaacca acatgaagca tgtggcaggc gccgctgcag   8880
ctggggcagt ggtagggggc ctcggcggtt acatgctggg gagtgccatg agcagacccc   8940
tgatacactt tggcagtgac tatgaggacc gttactatcg tgaaaacatg taccgttacc   9000
ccaaccaagt gtactacagg ccagtggatc agtacagcaa ccagaacagt tttgtgcatg   9060
actgcgtcaa catcaccgtc aagcagcaca cagtgaccac gaccaccaag ggggagaact   9120
tcaccgagac ggacgtcaag atgatagagc gcgtggtgga acagatgtgc atcacccagt   9180
accagaaaga gtacgaggcg tacgcccaaa gaggggccag tgtgatcctc ttctcctccc   9240
ctcctgtgat cctcctcatc tctttcctcc ttttcctcat agtgggctga gggtggcctt   9300
tctgtcggca tcatcttctt aatctttatc aggttggggg agggaatatc tacctgcagc   9360
cctttagtgg tggtgtctca ttcttgcttc tctcttcggc acccataggc taacatccat   9420
ggcgcttgta gcactggaaa aggagagtag acctgagatg tgatgtattt aagccccatt   9480
tgattgaatc cttcataggc cagtgctagt gctggactgg taagagcgta acagcaaata   9540
atcattggtt gatctgggct catttttttgt ctggtgcaac agattgaggc taaaacaatt   9600
ctcaaaacac acttcaagta cctttaccta aatacctcca gctccttctc cagctagagc   9660
tcagtacaca aatgccccgc catagtagtg attttgtagc aactttccca tttaagaaaa   9720
cctgactaca ttttcctgtt caaatagcat ttctactgag ttggggagga ggccacataa   9780
tactcattca aaaaaatgaa actggaaatc cttagctcct gggcccaggg tcagcccagt   9840
ggaaagcatg tgtcctgtgt ctgcagagaa ctaaggatat tttgcaattt gcagtacagg   9900
ttacacagca gctattgcat caagaatgga tgtctgtgca acactagact tctgggcaga   9960
gggcattttc acaggcaatg aacataactc acataatatg aaaggctctg aaacttaaaa  10020
aattcccacc tgtgtgagga accctcagag gcagccttct gttatggatg tttaaagcac  10080
cttcatgggg tagttctttc tttagtaata caaactatag ataattaagg tagtaggaca  10140
tgaaacaatc ttctggacat tgagaacaaa tctcttttgt ttgtttatct gggaactgga  10200
gtgattttgc catttcttgg atgaagccag gagattttaa catagaggaa gctgcagcta  10260
taaaaacatc atatttattc atttgattga gtctttcatg ggccagtgcc ggtgttgggc  10320
tagcaagcat atgataccaa atatagaggg ttatgaagaa aatgattagt gtacaaaaaa  10380
gagaaatgct tacatttctt tattgctgtg tcataattgt caaaaatcag aattaggtcc  10440
tcaatttcta taattggctt ttgaatcaaa gaataggaag gcattccccc ccaaaaaagt  10500
taaagatgat agaaatatga tccattcata ttaggaaaag aaattctggt actgttattt  10560
aaataaggca aaattattcc ctggattgtt tggtgttgtc acctagcaga tatacattac  10620
tcttctgcat tgttattggc ttgcactttg tgggtatcct atgtaaaaaa aatatatgta  10680
tatatatata ttgcatatga caaacttgga gattttggtt agagctgtta acatctgaat  10740
tatcaaatgc attacttgtt tttgtaaggt actaaatatt taataatact taaaggaaac  10800
ccttttgtgt ggtccttcgg cttacaatgt gcactgaata gttttgtata aggatccaga  10860
gtggcatttg aaattcgcat gtgctttata ttttctatat ttgtaacttt gcatgtactt  10920
gttttattgt attaaaagtt tataaatgtt tattatctga ctaaaattaa aacaggagct  10980
acaatgag                                                           10988
```

<210> SEQ ID NO 2
<211> LENGTH: 514
<212> TYPE: DNA
<213> ORGANISM: Sus scrofa

<400> SEQUENCE: 2
cttggcacag gggccctagg ccccataggt gctgatagcc ctcattatag ccccattagc 60
agagctgcca gggtccctac aagaaggtgc ctggttacaa gaattattac tttacttatt 120
tatgcaccat gtggaagttt ccaggctaga agtcgaatca gagatgtagc tgctggccta 180
cgccacagcc ataccagatc tgagctgcat ctgcgacctc accacagcac acggcaaggc 240
cagggatcga acccgcgtcc tcatggatac taatccatgg ctggtttctg ctgagtcatg 300
atgggaactc ccagaatcac aaaagctcaa agctgtggca aacccaccag gtgtttattg 360
gtttttccag tttagataca atgtatcaag cagaggttat ttttaccata agcatgttgc 420
tggcattcca cctttatctt ttctaagaaa cagagccaga aaattatctg aaggtcaaat 480
ttgtccttag agaaggagaa agagttgagt taac 514

<210> SEQ ID NO 3
<211> LENGTH: 1019
<212> TYPE: DNA
<213> ORGANISM: Sus scrofa

<400> SEQUENCE: 3
cggttacatg ctggggagtg ccatgagcag acccctgata cactttggca gtgactatga 60
ggaccgttac tatcgtgaaa acatgtaccg ttaccccaac caagtgtact acaggccagt 120
ggatcagtac agcaaccaga acagttttgt gcatgactgc gtcaacatca ccgtcaagca 180
gcacacagtg accacgacca ccaaggggga gaacttcacc gagacggacg tcaagatgat 240
agagcgcgtg gtggaacaga tgtgcatcac ccagtaccag aaagagtacg aggcgtacgc 300
ccaaagaggg gccagtgtga tcctcttctc ctcccctcct gtgatcctcc tcatctcttt 360
cctccttttc ctcatagtgg gctgagggtg gcctttctgt cggcatcatc ttcttaatct 420
ttatcaggtt gggggaggga atatctacct gcagcccttt agtggtggtg tctcattctt 480
gcttctctct tcggcaccca taggctaaca tccatggcgc ttgtagcact ggaaaaggag 540
agtagacctg agatgtgatg tatttaagcc ccatttgatt gaatccttca taggccagtg 600
ctagtgctgg actggtaaga gcgtaacagc aaataatcat tggttgatct gggctcattt 660
tttgtctggt gcaacagatt gaggctaaaa caattctcaa aacacacttc aagtaccttt 720
acctaaatac ctccagctcc ttctccagct agagctcagt acacaaatgc cccgccatag 780
tagtgatttt gtagcaactt tcccatttaa gaaaacctga ctacattttc ctgttcaaat 840
agcatttcta ctgagttggg gaggaggcca cataatactc attcaaaaaa atgaaactgg 900
aaatccttag ctcctgggcc cagggtcagc ccagtggaaa gcatgtgtcc tgtgtctgca 960
gagaactaag gatattttgc aatttgcagt acaggttaca cagcagctat tgcatcaag 1019

<210> SEQ ID NO 4
<211> LENGTH: 720
<212> TYPE: DNA
<213> ORGANISM: Sus scrofa

<400> SEQUENCE: 4
atggtgagca agggcgagga gctgttcacc ggggtggtgc ccatcctggt cgagctggac 60
ggcgacgtga acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240

-continued

```
cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actcacggca tggacgagct gtacaagtaa    720


<210> SEQ ID NO 5
<211> LENGTH: 29
<212> TYPE: DNA
<213> ORGANISM: Sus scrofa

<400> SEQUENCE: 5

ctagacgcgt cttggcacag gggccctag                                       29


<210> SEQ ID NO 6
<211> LENGTH: 30
<212> TYPE: DNA
<213> ORGANISM: Sus scrofa

<400> SEQUENCE: 6

gactacgtac gcctaccact gccccagctg                                      30


<210> SEQ ID NO 7
<211> LENGTH: 29
<212> TYPE: DNA
<213> ORGANISM: Sus scrofa

<400> SEQUENCE: 7

gactctcgag cggttacatg ctggggagt                                       29


<210> SEQ ID NO 8
<211> LENGTH: 31
<212> TYPE: DNA
<213> ORGANISM: Sus scrofa

<400> SEQUENCE: 8

gtcaggcgcg ccttgatgca atagctgctg t                                    31


<210> SEQ ID NO 9
<211> LENGTH: 20
<212> TYPE: DNA
<213> ORGANISM: Sus scrofa

<400> SEQUENCE: 9

ccagctgggg ctcgactaga                                                 20


<210> SEQ ID NO 10
<211> LENGTH: 22
<212> TYPE: DNA
<213> ORGANISM: Sus scrofa

<400> SEQUENCE: 10

ccattttgag cagcctcatt tg                                              22


<210> SEQ ID NO 11
<211> LENGTH: 34
```

-continued

<212> TYPE: DNA
<213> ORGANISM: Sus scrofa

<400> SEQUENCE: 11
ataacttcgt ataatgtatg ctatacgaac ggta 34

<210> SEQ ID NO 12
<211> LENGTH: 184
<212> TYPE: DNA
<213> ORGANISM: Sus scrofa

<400> SEQUENCE: 12
ggtggcagaa ggagtggata aagaggcaaa attgcctgcc aaaaagaaaa gaaagaaggg 60
tttgcgaatt ctaccgttcg tatagcatac attatacgaa gttatagggg aaaaggcgac 120
gaaagaaact gatccttgca aaaaagttta gtaaggattt gggatctggg aggcctgttg 180
caag 184

<210> SEQ ID NO 13
<211> LENGTH: 67
<212> TYPE: DNA
<213> ORGANISM: Sus scrofa

<400> SEQUENCE: 13
agaagggttt gcgaattcta ccgttcgtat agcatacatt atacgaagtt ataggggaaa 60
aggcgac 67

<210> SEQ ID NO 14
<211> LENGTH: 71
<212> TYPE: DNA
<213> ORGANISM: Sus scrofa

<400> SEQUENCE: 14
ggtggcagaa ggagtggata aagaggcaaa attgcctgcc aaaaagaaaa gaaagaaggg 60
tttgcgaatt c 71

<210> SEQ ID NO 15
<211> LENGTH: 79
<212> TYPE: DNA
<213> ORGANISM: Sus scrofa

<400> SEQUENCE: 15
aggggaaaag gcgacgaaag aaactgatcc ttgcaaaaaa gtttagtaag gatttgggat 60
ctgggaggcc tgttgcaag 79

<210> SEQ ID NO 16
<211> LENGTH: 65
<212> TYPE: DNA
<213> ORGANISM: Sus scrofa

<400> SEQUENCE: 16
agaagggttt gcgaatccta ccgttcgtat gcatacatta tacgaagtta aggggaaaag 60
gcgac 65

<210> SEQ ID NO 17
<211> LENGTH: 65
<212> TYPE: DNA
<213> ORGANISM: Sus scrofa

<400> SEQUENCE: 17

-continued

```
agaagggttt gcgaattcta ccgttcgtat gcatacatta tacgaagtta aggggaaaag     60

gcggc                                                                 65
```